(12) United States Patent
Zhang et al.

(10) Patent No.: US 11,551,341 B2
(45) Date of Patent: Jan. 10, 2023

(54) METHOD AND DEVICE FOR AUTOMATICALLY DRAWING STRUCTURAL CRACKS AND PRECISELY MEASURING WIDTHS THEREOF

(71) Applicant: SOUTHEAST UNIVERSITY, Jiangsu (CN)

(72) Inventors: Jian Zhang, Jiangsu (CN); Futao Ni, Jiangsu (CN)

(73) Assignee: SOUTHEAST UNIVERSITY, Jiangsu (CN)

( * ) Notice: Subject to any disclaimer, the term of this patent is extended or adjusted under 35 U.S.C. 154(b) by 54 days.

(21) Appl. No.: 16/765,871

(22) PCT Filed: Mar. 6, 2018

(86) PCT No.: PCT/CN2018/078104
§ 371 (c)(1),
(2) Date: May 21, 2020

(87) PCT Pub. No.: WO2019/134252
PCT Pub. Date: Jul. 11, 2019

(65) Prior Publication Data
US 2020/0364849 A1    Nov. 19, 2020

(30) Foreign Application Priority Data

Jan. 3, 2018  (CN) .......................... 201810006120.0

(51) Int. Cl.
*G06T 7/00* (2017.01)
*G06T 7/70* (2017.01)
(Continued)

(52) U.S. Cl.
CPC .......... *G06T 7/0004* (2013.01); *G01B 11/022* (2013.01); *G01N 33/383* (2013.01);
(Continued)

(58) Field of Classification Search
CPC ....... G06T 7/00; G06T 7/0002; G06T 7/0004; G06T 7/62; G06T 7/60; G06T 7/70;
(Continued)

(56) References Cited

U.S. PATENT DOCUMENTS

| 10,520,298 B2 * | 12/2019 | Chen ................... G01M 5/0033 |
| 2019/0331301 A1 * | 10/2019 | Du ...................... G01M 5/0033 |
| 2020/0098103 A1 * | 3/2020 | Chen ................... G06T 7/0006 |

FOREIGN PATENT DOCUMENTS

| CN | 101957178 | 1/2011 |
| CN | 103455985 A * | 12/2013 |

(Continued)

OTHER PUBLICATIONS

B. Cornelis, Y. Yang, J. T. Vogelstein, A. Dooms, I. Daubechies and D. Dunson, "Bayesian crack detection in ultra high resolution multimodal images of paintings," 2013 18th International Conference on Digital Signal Processing (DSP), 2013, pp. 1-8, doi: 10.1109/ICDSP.2013.6622710. (Year: 2013).*

(Continued)

Primary Examiner — Andrew M Moyer
Assistant Examiner — Stephen M Brinich
(74) Attorney, Agent, or Firm — JCIPRNET

(57) ABSTRACT

The present invention discloses a method and device for automatically drawing structural cracks and precisely measuring widths thereof. The method comprises a method for automatically drawing cracks and a method for calculating widths of these cracks based on a single-pixel skeleton and Zernike orthogonal moments, wherein the method for automatically drawing cracks is used to rapidly and precisely draw cracks in the surface of a structure, and the method for calculating widths of these cracks based on a single-pixel (Continued)

skeleton and Zernike orthogonal moments is used to calculate widths of macro-cracks and micro-cracks in an image in a real-time manner.

5 Claims, 14 Drawing Sheets

(51) Int. Cl.
```
G06T 5/00      (2006.01)
G06T 5/20      (2006.01)
G06T 7/80      (2017.01)
G06T 7/136     (2017.01)
G06T 7/62      (2017.01)
G01B 11/02     (2006.01)
G01N 33/38     (2006.01)
G06T 11/00     (2006.01)
```
(52) U.S. Cl.
CPC ............... *G06T 5/002* (2013.01); *G06T 5/20* (2013.01); *G06T 7/136* (2017.01); *G06T 7/62* (2017.01); *G06T 7/70* (2017.01); *G06T 7/80* (2017.01); *G06T 11/00* (2013.01); *G06T 2207/30132* (2013.01); *G06T 2207/30244* (2013.01)
(58) Field of Classification Search
CPC .... G06T 7/73; G06T 7/75; G06T 7/80; G06T 7/13; G06T 7/136; G06T 5/002; G06T 5/20; G06T 11/00; G06T 2207/30132; G06T 2207/30136; G06T 2207/30141; G06T 2207/30148; G06T 2207/30152; G06T 2207/30244; G01B 11/02; G01B 11/022; G01N 33/38; G01N 33/383; G01N 33/385; G01N 33/386; G01N 33/388
USPC ................ 382/103, 100, 141–142, 145–152
See application file for complete search history.

(56) References Cited

FOREIGN PATENT DOCUMENTS

| CN | 105719283 | 6/2016 |
|---|---|---|
| CN | 106651872 | 5/2017 |
| CN | 106910186 | 6/2017 |
| CN | 107133960 | 9/2017 |
| CN | 107480611 | 12/2017 |
| KR | 101772916 | 8/2017 |

OTHER PUBLICATIONS

G. Xiaozheng, L. Huan, Z. Guangbin and Y. Wenjie, "Study on surface crack detection of low voltage current transformer," 2017 29th Chinese Control and Decision Conference (CCDC), 2017, pp. 7748-7752, doi: 10.1109/CCDC.2017.7978598. (Year: 2017).*

S. Chaudhury, G. Nakano, J. Takada and A. Iketani, "Spatial-Temporal Motion Field Analysis for Pixelwise Crack Detection on Concrete Surfaces," 2017 IEEE Winter Conference on Applications of Computer Vision (WACV), 2017, pp. 336-344, doi: 10.1109/WACV.2017.44. (Year: 2017).*

L. Zhang, G. Zhou, Y. Han, H. Lin and Y. Wu, "Application of Internet of Things Technology and Convolutional Neural Network Model in Bridge Crack Detection," in IEEE Access, vol. 6, pp. 39442-39451, 2018, doi: 10.1109/ACCESS.2018.2855144. (Year: 2018).*

Hoang, Nhat-Duc. (2018). "Image Processing-Based Recognition of Wall Defects Using Machine Learning Approaches and Steerable Filters." Computational Intelligence and Neuroscience. 2018. 1-18. 10.1155/2018/7913952. (Year: 2018).*

V. Vijayan, C. M. Joy and S. S, "A Survey on Surface Crack Detection in Concretes using Traditional, Image Processing, Machine Learning, and Deep Learning Techniques," 2021 Int'l Conf on Communication, Control and Information Sciences (ICCISc), 2021, pp. 1-6, doi: 10.1109/ICCISc52257.2021.9484914. (Year: 2021).*

\* cited by examiner

| 0      | 0.0225  | 0.0394  | 0.0396  | 0.0394  | 0.0225  | 0      |
|--------|---------|---------|---------|---------|---------|--------|
| 0.0225 | 0.0271  | -0.0128 | -0.0261 | -0.0128 | 0.0271  | 0.0225 |
| 0.0394 | -0.0128 | -0.0528 | -0.0661 | -0.0528 | -0.0128 | 0.0394 |
| 0.0396 | -0.0261 | -0.0661 | -0.0794 | -0.0661 | -0.0261 | 0.0396 |
| 0.0394 | -0.0128 | -0.0528 | -0.0661 | -0.0528 | -0.0128 | 0.0394 |
| 0.0225 | 0.0271  | -0.0128 | -0.0261 | -0.0128 | 0.0271  | 0.0225 |
| 0      | 0.0225  | 0.0394  | 0.0396  | 0.0394  | 0.0225  | 0      |

(a) Template M20

| 0      | 0.0130  | 0.0056  | -0.0018 | 0.0056  | 0.0130  | 0      |
|--------|---------|---------|---------|---------|---------|--------|
| 0.0130 | -0.0186 | -0.0323 | -0.0239 | -0.0323 | -0.0186 | 0.0130 |
| 0.0056 | -0.0323 | 0.0125  | 0.0406  | 0.0125  | -0.0323 | 0.0056 |
| -0.0018| -0.0239 | 0.0406  | 0.0751  | 0.0406  | -0.0239 | -0.0018|
| 0.0056 | -0.0323 | 0.0125  | 0.0406  | 0.0125  | -0.0323 | 0.0056 |
| 0.0130 | -0.0186 | -0.0323 | -0.0239 | -0.0323 | -0.0186 | 0.0130 |
| 0      | 0.0130  | 0.0056  | -0.0018 | 0.0056  | 0.0130  | 0      |

(b) Template M40

FIG. 7

METHOD AND DEVICE FOR AUTOMATICALLY DRAWING STRUCTURAL CRACKS AND PRECISELY MEASURING WIDTHS THEREOF

CROSS-REFERENCE TO RELATED APPLICATION

This application is a 371 of international application of PCT application serial no. PCT/CN2018/078104, filed on Mar. 6, 2018, which claims the priority benefit of China application no. 201810006120.0, filed on Jan. 3, 2018. The entirety of each of the above mentioned patent applications is hereby incorporated by reference herein and made a part of this specification.

BACKGROUND

Technical Field

The present invention relates to the field of structure detection and evaluation, and in particular to a method and device for detecting structural cracks on a surface based on digital image processing.

Description of Related Art

In the field of civil engineering structure, the test for bearing capacity of a new material or structure is one of the experimental methods that are most widely used. Besides structural response indexes such as structural strain and deformation, the development of a structural crack, having a clear correspondence to the bearing capacity of a structure, is an important part of a structural bearing capacity test. However, at present, cracks are mainly observed manually, and drawn by a person with interrupting an experiment, and widths of the cracks are measured by manually attaching a crack width gauge to the surface of a structure. In addition, crack condition is one of the main indexes for periodic structure inspection, load test and laboratory experiment. Manually drawing cracks and measuring crack widths with a crack width gauge affects the progress of an experiment due to low efficiency as well as a waste of time and energy, and also lead to a detection result of great personal error.

In recent years, the concrete crack detection technology based on digital image processing, which can overcome disadvantages of conventional manual detection, such as a waste of time and energy as well as inadequate detection precision, has become a hotspot for research of crack detection technologies at home and abroad. Common image-based crack identification methods include edge detection, threshold segmentation and so on. For example, a method and system for pavement crack identification based on Prewitt operator disclosed in Chinese Patent Publication No. CN 106651872A and a method for pavement crack image detection based on Hessian matrix multi-scale filtering disclosed in Chinese Patent Publication No. CN 105719283 are all based on conventional image processing algorithms, however, as the background and features of a crack have considerable variability and complexity, it is difficult to determine whether it is a crack according to features identified by a conventional algorithm. Moreover, a conventional algorithm tends to require more human intervention, thereby resulting in a low automation level.

Since Hinton published an article in Science in 2006, more and more attention has been paid to deep learning. Deep learning has achieved amazing success in image recognition and has also started to be applied to crack identification based on image processing. Abroad, Cha, Young-Jin and others have applied deep learning to crack identification based on image processing. In China, Chinese Patent Publication No. CN 106910186A discloses a method for detecting and locating bridge cracks based on CNN deep learning, which can hardly meet the requirements for detecting cracks of different widths in an image due to adopting CNN templates of only 16 pixels in size, and cannot output binary images of cracks accurate to pixel level. Chinese Patent Publication No. CN 107133960A discloses an image crack segmentation method based on a deep convolutional neural network, which utilizes a feature map obtained by the convolutional network as an input to carry out crack region segmentation. As the size of a pixel block is generally much smaller than the size of the whole image, the size of the pixel block will limit the size of a sensed region, and only some local features can be extracted. Therefore, this method has disadvantages such as limited performance of classifying, poor sensitivity of an identification result to details in an image, and a detection result of inadequate precision due to a fuzzy crack edge. The method can hardly be applied to real projects.

Moreover, all conventional crack width measurement methods based on digital image processing calculate crack width as the distance between two pixels, and thus have great limitations. For example, Chinese Patent Publication No. CN 106018411A discloses a method and device for measuring crack width, wherein crack width is measured by calculating the resolution of an image according to the size of a laser spot emitted by a laser in the image and then multiplying the resolution by the distance between two pixels. Chinese Patent Publication No. CN 104089580A discloses an instrument and method for measuring width of a crack on a concrete surface based on a smartphone, wherein crack width is measured by calculating a pixel resolution by a manual marking method, and then multiplying the resolution by an average distance obtained from "pixel counting" between two edges. Crack width measurement methods based on "pixel counting" in the past are often applicable to macro-cracks in images and can work well. However, for micro-cracks (smaller than 5 pixels) in images, these methods have great identification errors and can hardly meet requirements for measurement precision.

In general, crack condition is an important detection index for periodic structure inspection, laboratory experiments and other projects. The method for manually drawing cracks is time-consuming and laborious, and has a great error in measurement of crack width. Moreover, there are still great defects in crack detection based on image processing. These defects are specifically as follows: (1) the conventional automatic crack drawing technology based on image processing tends to require excessive human interference, so that the automation level is low and cracks cannot be effectively distinguished from noise interferences, and although the existing image crack identification technology based on deep learning has achieved some success, it still cannot meet requirements for automatically and precisely drawing a crack; and (2) the calculated width of a micro-crack in an image is of great error, and it needs to sacrifice the size of the field of view to meet requirements for detection precision.

SUMMARY

The present invention discloses a method and device for automatically drawing structural cracks and precisely measuring widths thereof to solve technical problems existing in the prior art. The method aims at rapidly and automatically drawing structural cracks and precisely measuring widths thereof. While automatically drawing cracks in an image with high precision, high accuracy and high recall, the method can accurately measure widths of both macro-cracks and micro-cracks smaller than 5 pixels in the image.

In order to achieve the aforementioned objects, the overall idea of the present invention is as follows:

A method for automatically drawing structural cracks comprises the following steps: 1) detecting, by a crack detection method based on multi-scale deep learning, a crack range in an image using multi-scale deep learning to ensure that no crack information is missed for subsequent work; 2) extracting, by a preliminary crack extraction method of "global-local co-segmentation" based on deep learning, median filtering and Hessian matrix-based linear enhancement, full information of both macro-cracks and micro-cracks in the image to ensure a detection result of high recall; and 3) effectively removing, by a fine crack detection method based on deep learning, image segmentation and image reconstruction, noise from the result to ensure a detection result of high accuracy and precision.

As an improvement of the present invention, the crack detection method based on multi-scale deep learning in step 1) is specifically as follows:

Because concrete cracks are complex and diversified in morphology, single-scale deep learning often cannot meet requirements for detecting cracks of different widths in an image, and crack information in an image can be easily missed in the analysis based on detection results of single-scale deep learning. With deep learning models of multiple scales from large to small, the large-scale deep learning modules are first adopted to scan and detect the whole image; and on the basis that a crack range has been determined by the large-scale (224*224*3) deep learning modules, a small-scale (32*32*3) deep learning module is adopted to scan and detect the window of a crack detected by each large-scale deep learning module.

As an improvement of the present invention, for detection by a large-scale deep learning model, because the input of the model is a 224*224*3 image and the image size will not exactly be an integral multiple of 224, scaling the image will result in loss of information in the image. Therefore, during scanning and detection, windows for each layer start from four right angles and slide to a center by 112 pixels each time in x and y directions, wherein the center refers to the intersection of x axis and y axis that lead to an image symmetry, and scanning windows for one layer are encrypted to ensure that the whole image can be scanned in a partially overlapping manner and a range containing all cracks is output; and for each detected 224*224 window containing a crack, a small-scale deep learning model (32*32*3) is adopted to scan and detect each 224*224 image in a manner of sliding 16 pixels each time in x and y directions respectively.

As an improvement of the present invention, on the basis of a narrowed range of crack detection based on multi-scale deep learning, direct threshold segmentation will still lead to loss of micro-crack information. On the basis of a crack detection range based on multi-scale deep learning, a method that combines median-filtered image subtraction, 1-scale Hessian matrix-based linear enhancement and Otsu threshold segmentation is employed to carry out the preliminary crack extraction. The extracted information can contain full information of both macro-cracks and micro-cracks in an image.

The preliminary crack extraction method of "global-local co-segmentation" in step 2) is specifically as follows:

21) Within each 224*224 window where a crack is detected, the original image is converted into a gray-scale image and then processed by large-scale median filtering, the filtered image is subtracted from the original image to obtain a new image, and Otsu adaptive threshold segmentation is applied to the new image to obtain a binary image img1 of the crack.

22) The original image is processed by small-scale median filtering, and the filtered image is subtracted from the original image to obtain a new image, and then the linear portion of the new image is enhanced by a Hessian matrix-based image enhancement method, wherein the Hessian matrix at each point of the image $$I(x) \text{ is } \nabla^2 I(x) = \begin{bmatrix} I_{xx}(x) & I_{xy}(x) \\ I_{yx}(x) & I_{yy}(x) \end{bmatrix},$$

eigenvalues of the Hessian matrix at each point is calculated as $\lambda_1$ and $$\lambda_2, \lambda_{12} = \begin{cases} |\lambda_2|\left(1 + \dfrac{\lambda_1}{|\lambda_2|}\right) = |\lambda_2| + \lambda_1 & \text{if } \lambda_2 \le \lambda_1 \le 0 \\ |\lambda_2|\left(1 - \alpha\dfrac{\lambda_1}{|\lambda_2|}\right) = |\lambda_2| - \alpha\lambda_1 & \text{if } \lambda_2 < 0 < \lambda_1 < \dfrac{|\lambda_2|}{\alpha}, \\ 0 & \text{otherwise} \end{cases}$$

$R(x) = \lambda_{12}(x)$ is defined as the enhanced image, and $\alpha=0.25$. Otsu adaptive threshold segmentation is applied to the enhanced image within each 32*32 window of a crack detected by the small-scale deep learning model, and a binary image img2 of the crack is obtained after uniting.

23) The binary image img1 and the binary image img2 are united to obtain an output crack binary image for the 224*224 window.

24) The output binary image results for all detected 224*224 windows containing cracks in the first step are united to obtain a preliminary crack extraction result for the whole image.

As an improvement of the present invention, the fine crack detection method based on deep learning, image segmentation and image reconstruction in step 3) is specifically as follows:

As the preliminarily-extracted crack binary image will contain a lot of noise information, the proposed image segmentation method based on a single-pixel crack skeleton is utilized to segment the preliminarily-extracted crack image at two levels, and an image reconstruction method, in connection with deep learning, is utilized to perform single-factor analysis on the segmented cracks to determine whether they are cracks, ultimately realizing the fine extraction of cracks.

The image segmentation method based on a single-pixel skeleton is conducted at two levels. The skeleton is first segmented according to connectivity, portions of the crack binary image that each corresponds to one independent connected component are extracted respectively, and then each remaining connected component is further segmented into independent portions with endpoint and node information collected from the single-pixel crack skeleton, and the first level of segmentation can be implemented by utilizing the connectivity of the initial crack binary image.

The second level of segmentation is specifically as follows:

A pixel on the skeleton that has only one of its eight neighbors on the skeleton is defined as an endpoint, and a pixel that has more than three of its eight neighbors on the skeleton is defined as a node, and on the basis of each independent connected component skeleton, the binary image output at the previous level is further segmented, with the endpoint and node information of a single pixel, into independent portions as outputs of this level, and the method for segmenting an independent connected component includes the following operations:

a. An eight-neighbor rule is utilized to identify endpoints and nodes on the skeleton, segmentation is terminated when there are only endpoints and no node on the skeleton, and the corresponding regions in the initial crack binary image are directly output.

b. The nodes on the connected component are deleted, by utilizing the endpoint and node information, to obtain independent skeleton segments, the length of each skeleton segment is calculated, and a threshold T is set as 32.

c. As other interferences on cracks often occur in the form of skeleton branches, for each segmented skeleton segment that contains one endpoint for the original skeleton, regardless of whether the length of the skeleton segment is lower than the threshold, a circle is drawn, with a radius of ten pixels and a center at the node, to obtain intersections with other skeleton branches of the same node, the region of the skeleton is determined with the angle bisector of each branch of the node and the outline of the initial crack binary image, and independent crack binary regions are obtained from segmentation and filling by a region growing algorithm.

d. For a skeleton segment has a length greater than the threshold T and two ends as nodes on the original skeleton, a circle is drawn, with a radius of ten pixels and a center at the node, to obtain intersections with other skeleton branches of the same node, the region of the skeleton is determined with the angle bisector of the node and the outline of the original binary image, and independent crack binary regions are obtained from segmentation and filling by a region growing algorithm.

e. If the length of the extracted skeleton is less than the threshold, the center of the skeleton is determined, and an initial crack binary image having a length and width as T around the center of the skeleton segment is directly captured as a segmented image.

A single-factor analysis is performed, by the image reconstruction method in combination with deep learning, on the segmented cracks, and a new fine detection image that contains separately-segmented crack information but contains no other interference information needs to be constructed for fine crack detection of each segmented independent region.

As an improvement of the present invention, the specific method for constructing a fine detection image in step 3) is as follows:

a. After an initial crack binary image is obtained, the region corresponding to the initial crack binary image is removed from the original image.

b. The removed region of the original image is filled with the average value of the three-channel (RGB) values of pixels around each connected component of the initial crack binary image, and the edge is removed by median filtering to construct a new image.

c. For images segmented from a crack binary image based on a single-pixel skeleton at two levels, binary connected components are extracted, and the length of a bounding rectangle of each connected component is calculated.

d. A fine detection image is constructed with the original image, the new image and the range of the bounding rectangles of connected components, that is, each independent segmented crack binary image region is filled with the value of the original image and a region outside the segmented crack binary image region is filled with the value of the new image to obtain a constructed detection image, wherein the specific rule is as follows: if the length of the bounding rectangle is less than or equal to 32, a detection image is constructed with the original image and the new image within a range of 32*32 around the center, and is scaled to the size of 224*224; if the length of the bounding rectangle is greater than 32 but less than 96, a new image is constructed within a range of the length of the bounding rectangle around the center, and is scaled to the size of 224*224; if the length of the bounding rectangle is greater than 96 but less than 224, a 224*224 image is directly constructed around the center with the new image and the original image; and if the length of the bounding rectangle is greater than 224, a detection image is constructed within a range of 224 pixels expanding outwardly from the bounding rectangle around the center.

After a constructed detection image for the segmented crack is obtained, detection based on deep learning is performed once again to carry out single-factor analysis on the segmented cracks, thus achieving the purpose of fine extraction. The constructed detection images are also divided into two levels according to the two levels of the segmentation method based on the single-pixel skeleton. The specific method for scanning and detecting the constructed fine detection image with deep learning is as follows:

a. For images constructed at two levels, if the image size is less than or equal to 224*224*3, the image is enlarged to the size of 224*224*3, and then detected with a deep learning model to directly determine whether a crack is contained therein.

b. For constructed detection images with a size larger than 224*224*3, corresponding crack skeletons are extracted, and grids equidistantly spaced by 32 pixels in x and y directions are constructed, and a new image is scanned and detected with a intersections of a skeleton and a checkerboard as a center, wherein some of the intersections should be removed, so that the distance between every two intersections is larger than 16 pixels. The detection results are analyzed statistically. For constructed images at the first level, if the proportion of detection results representing that cracks are contained is greater than 0.2, then it is considered that cracks are contained. For constructed images at the second level, if the proportion of detection results representing that cracks are contained is greater than 0.8, then it is considered that cracks are contained.

After three steps including crack range detection based on multi-scale deep learning, preliminary crack binary image extraction and fine crack detection, a crack binary image having high precision, high accuracy and high recall can be obtained.

The present invention provides a method for precisely measuring crack widths based on a single-pixel crack skeleton and Zernike orthogonal moments.

Conventional methods for calculating crack widths, which calculate the distance between two pixels by "pixel counting", works badly in calculating the width of a crack less than 5 pixels. Therefore, for cracks smaller than 5 pixels in images, the present invention proposes a method for calculating crack widths based on a single-pixel skeleton and Zernike orthogonal moments.

The method for calculating crack widths based on a single-pixel skeleton and Zernike orthogonal moments utilizes a single-pixel skeleton to determine a rotation angle for an image. The image at this point is rotated, symmetrized and mirrored to obtain two images symmetrical with respect to the y coordinate axis. The second-order orthogonal moment $A'_{20}$ and the fourth-order orthogonal moment $A'_{40}$ are calculated respectively for the two symmetrical images by utilizing orthogonal moment templates. The widths of the two symmetrical images are respectively calculated by a formula $$2l = 2\sqrt{\frac{5A'_{40} + 3A'_{20}}{8A'_{20}}}.$$

An average value is taken as crack width (unit: pixel) at this point after two error corrections are performed, and a final width of the crack at this point is obtained according to a pixel resolution (mm/pixel). It is worth noting that the method proposed by the present invention actually calculates an average width of a crack within an orthogonal moment template range at a certain point on an image.

1) A single-pixel crack skeleton around a width calculation point is extracted, a rotation angle is determined for the image, an image within a range of 13*13 pixels around the width calculation point is captured, and preprocessing 1 is performed to obtain a gray-scale image (0-1) of the image, a matrix, with all elements of 13*13 being 1, is subtracted from the gray-scale image, so that the gray value of a crack pixel in the image is high and the gray value of a background pixel is low, and the maximum gray value MAX is recorded.

2) The image is rotated according to the skeleton direction, mirroring operations are respectively performed, with the column where the accumulated pixel value of cracks is the highest after rotation (i.e., the brightest column) as a central column, to obtain two symmetrical images, and smooth filtering is vertically applied to the two images.

3) It is checked whether the images obtained from mirroring meet requirements for calculation (assuming that the line width is 5 and the brightest is column 2, if one of the images does not meet conditions for calculation after mirroring, further processing is required). The average gray value within the range of a central column template is set as L, and the average gray value of each column on either side of the central column is set as L1, L2, L3 and L4 in sequence, wherein three conditions are set as: |L4−L3|/|L2−L3|>=0.3, |L1−L4|/|L−L4|>=0.8, and |L4−L3|/|L−L4|>=0.1. If all the three conditions are met, the central column and one column on the left side of the central column are deleted, and Mark=2 is recorded, otherwise, Mark=0 is recorded, and preprocessing 2 is performed: a minimum gray value MIN within a range of 7*7 around the image center is found, and the MIN is subtracted from the image gray to construct a new image.

4) The existing orthogonal moment templates M20 and M40 are used instead of the formula to calculate corresponding orthogonal moments and thus calculate the width of a crack in the image; the first error correction is as follows: principle error correction values are calculated by interpolation according to the value of m=L1/L with reference to FIG. 8; the second error correction is as follows: the average gray value within the range of the central column template of the image is divided by the maximum gray value MAX of the original image subtracted by the recorded minimum gray value MIN to obtain a correction factor, and a Mark value is added to the corrected value to obtain a final crack width of each mirror image; and then an average value of the calculated widths of the two mirror images after the error corrections is taken as a final crack width.

A device for automatically drawing cracks of a concrete specimen and measuring widths thereof in a laboratory comprises an image calibration module, an image acquisition module, an image processing system, and a camera tripod.

The device for automatically drawing structural cracks and precisely measuring widths thereof can rapidly and automatically draw structural cracks on a surface and precisely measure crack widths.

The image calibration module is configured to correct the pose of a camera, calculate the resolution of an image, and paste a plurality of manually-printed checkerboards with a known size on the surface of a concrete specimen; the image acquisition module composed of a single lens reflex camera is mainly configured to acquire a high-resolution image of the concrete specimen for image processing in the next step; and the image processing system is embedded with an automatic crack drawing algorithm module, a crack feature analysis algorithm module, a calculation result storage module and a wireless transmission module, wherein the wireless transmission module is configured to wirelessly transmit a detection result and an original image to a client.

The automatic crack drawing algorithm module comprises a module for crack range detection based on multiscale deep learning, a module for preliminary crack extraction based on deep learning, median filtering and Hessian matrix-based linear enhancement, and a module for fine crack detection based on deep learning, image segmentation and image reconstruction, and can rapidly and automatically draw the acquired image with high precision, high accuracy and high recall, wherein the information of both macro-cracks and micro-cracks in the image is drawn.

The crack feature analysis algorithm module is configured to calculate crack widths, and includes the method for calculating crack widths based on a single-pixel skeleton and Zernike orthogonal moments proposed by the present invention, and this method can also achieve higher calculation precision for micro-cracks smaller than 5 pixels in an image, obviously superior to conventional algorithms in terms of calculation precision.

Compared with the prior art, the present invention has the following advantages. 1) The device developed by the present invention can be widely applied to the detection of structural cracks on a surface and the detection of cracks occurred on a surface in a laboratory structure test, and can output a precise crack binary image and precisely calculate the length, width and other features of a crack in just a few seconds; 2) The solution can rapidly, automatically and precisely draw a structural crack on a surface. The algorithm proposed by the present invention requires no human intervention to adjust the threshold segmentation coefficient and other coefficients, thereby resulting in a wide application range and a higher automation level. In addition, both macro-cracks and micro-cracks in the image can be identified as many as possible in a crack binary image output by the present invention, noise interferences, such as artificial marks and environmental pollution, can be removed effectively and precisely, and the identified crack binary image has high precision, high accuracy and high recall. 3) The solution can precisely measure the width of a structural crack on a surface. The method for measuring crack widths proposed by the present invention demonstrates a measurement precision significantly higher than a conventional method for measuring crack widths, especially for micro-cracks smaller than 5 pixels in images, and the error of width measurement for a micro-crack smaller than 5 pixels in an image can be controlled to be less than 10%. Meanwhile, this means that under the same measurement precision requirement, the method proposed by the present invention has a field of view nearly four times larger than that of a conventional method.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

FIG. 7 shows convolutional templates for calculating Zernike orthogonal moments in micro-crack width measurement according to the present invention.

DESCRIPTION OF THE EMBODIMENTS

In order to deepen the understanding of the present invention, the present examples will be described in detail below with reference to the accompanying drawings.

Example 1

Figure 3:
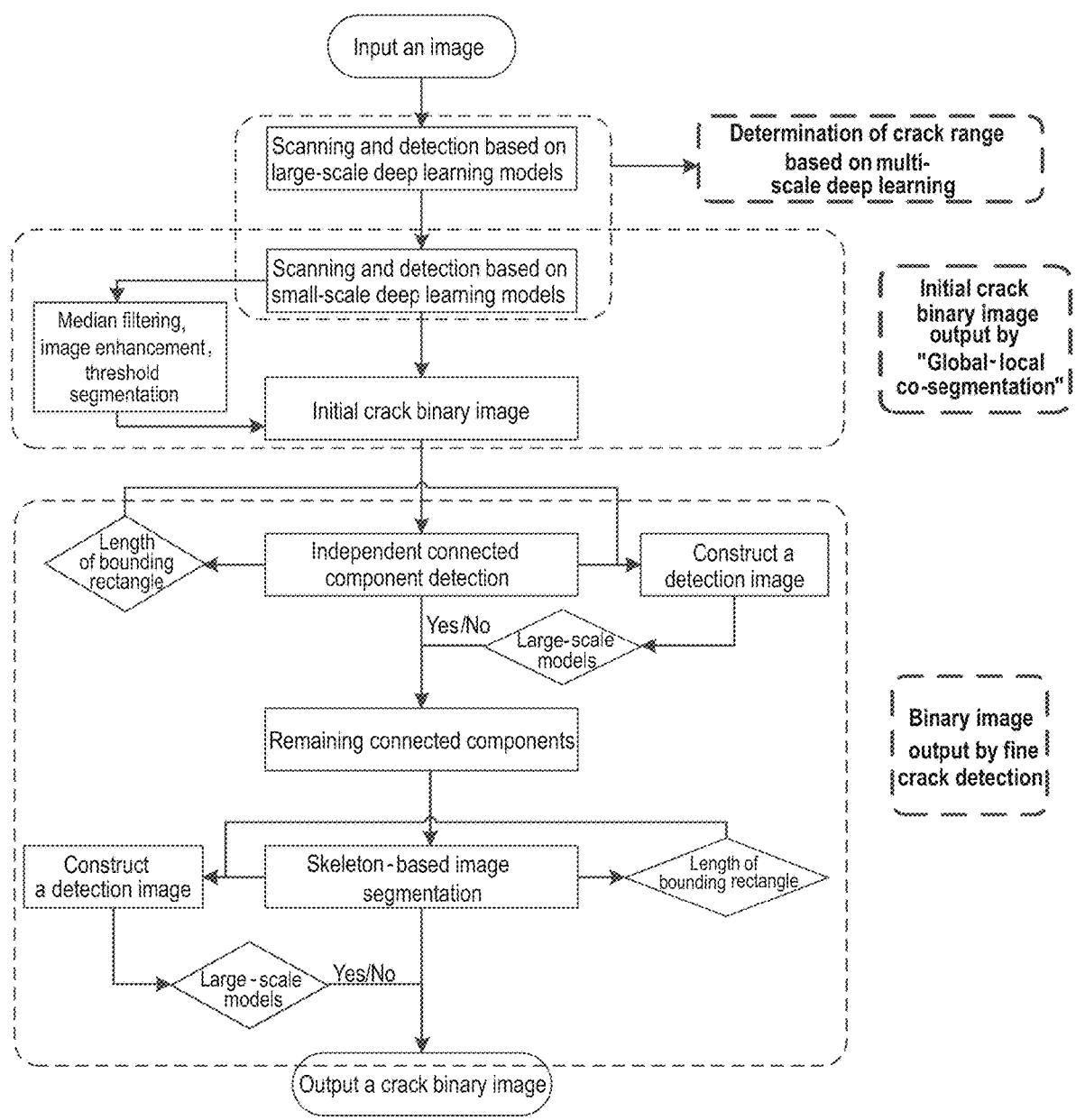
FIG. 3 is a diagram for a method for automatically drawing cracks according to the present invention.

A method for automatically drawing structural cracks As shown in FIG. 3, the method for automatically drawing structural cracks comprises the following steps: 1) detecting, by a crack detection method based on multi-scale deep learning, a crack range in an image using multi-scale deep learning to ensure that no crack information is missed for subsequent work; 2) extracting, by a preliminary crack extraction method of "global-local co-segmentation" based on deep learning, median filtering and Hessian matrix-based linear enhancement, full information of both macro-cracks and micro-cracks in the image to ensure a detection result of high recall; and 3) effectively removing, by a fine crack detection method based on deep learning, image segmentation and image reconstruction, noise from the result to ensure a detection result of high accuracy and precision. The crack detection method based on multi-scale deep learning in step 1) is specifically as follows: Because concrete cracks are complex and diversified in morphology, single-scale deep learning often cannot meet requirements for detecting cracks of different widths in an image, and crack information in an image can be easily missed in the analysis based on detection results of single-scale deep learning. With deep learning models of multiple scales from large to small, the large-scale deep learning modules are first adopted to scan and detect the whole image; and on the basis that a crack range has been determined by the large-scale (224*224*3) deep learning modules, a small-scale (32*32*3) deep learning module is adopted to scan and detect the window of a crack detected by each large-scale deep learning module. For detection by a large-scale deep learning model, because the input of the model is a 224*224*3 image and the image size will not exactly be an integral multiple of 224, scaling the image will result in loss of information in the image. Therefore, during scanning and detection, windows for each layer start from four right angles and slide to a center by 112 pixels each time in x and y directions, wherein the center refers to the intersection of x axis and y axis that lead to an image symmetry, and scanning windows for one layer are encrypted to ensure that the whole image can be scanned in a partially overlapping manner and a range containing all cracks is output; and for each detected 224*224 window containing a crack, a small-scale deep learning model (32*32*3) is adopted to scan and detect each 224*224 image in a manner of sliding 16 pixels each time in x and y directions respectively. On the basis of a narrowed range of crack detection based on multi-scale deep learning, direct threshold segmentation will still lead to loss of micro-crack information. On the basis of a crack detection range based on multi-scale deep learning, a method that combines median-filtered image subtraction, 1-scale Hessian matrix-based linear enhancement and Otsu threshold segmentation is employed to carry out the preliminary crack extraction. The extracted information can contain full information of both macro-cracks and micro-cracks in an image.

Figure 4:
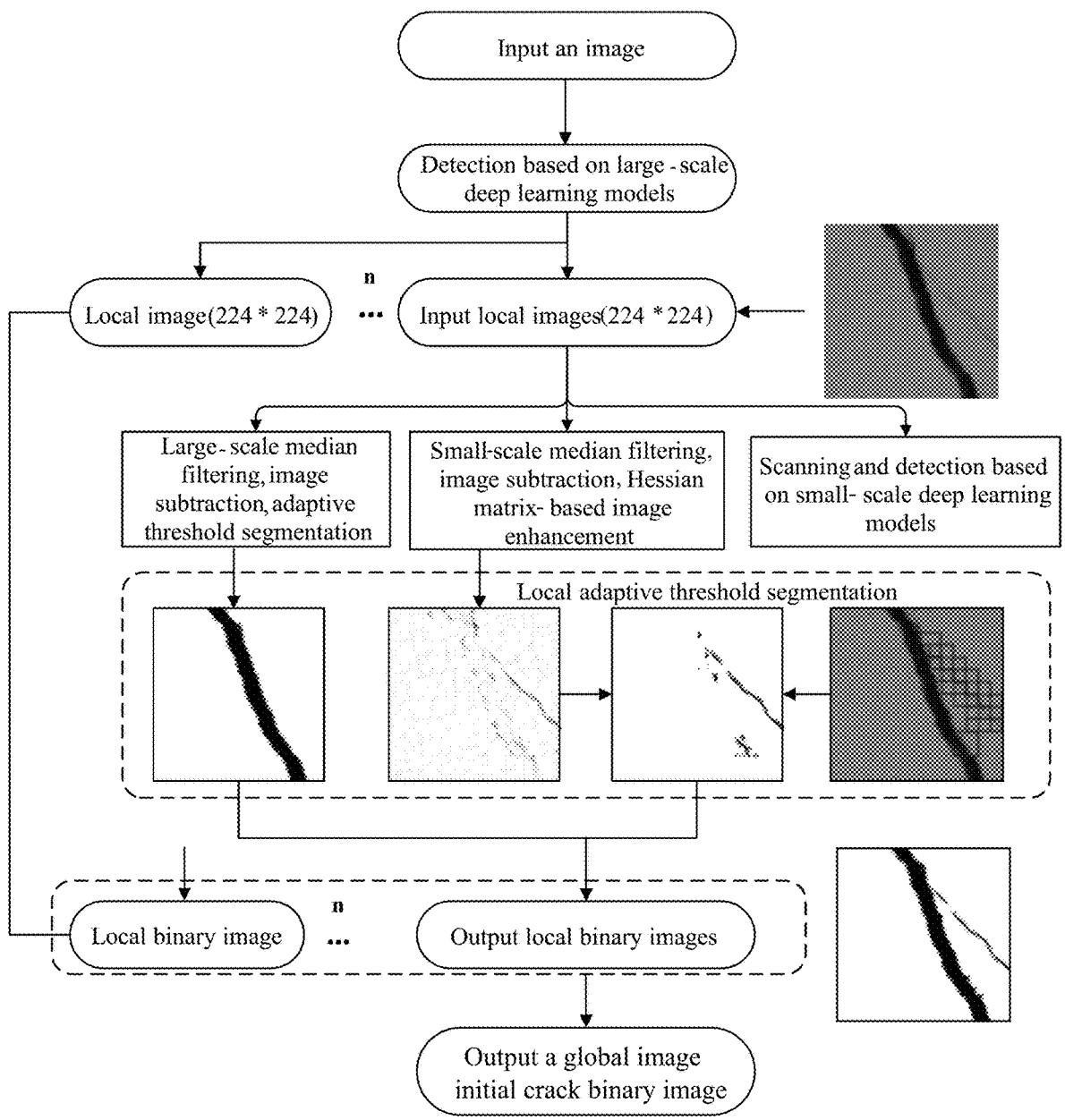
FIG. 4 is a diagram for a preliminary crack extraction method of "global-local co-segmentation" according to the present invention.

The preliminary crack extraction method of "global-local co-segmentation" in step 2) is shown in FIG. 4 and is specifically as follows:

21) Within each 224*224 window where a crack is detected, the original image is converted into a gray-scale image and then processed by large-scale median filtering, the filtered image is subtracted from the original image to obtain a new image, and Otsu adaptive threshold segmentation is applied to the new image to obtain a binary image img1 of the crack.

22) The original image is processed by small-scale median filtering, and the filtered image is subtracted from the original image to obtain a new image, and then the linear portion of the new image is enhanced by a Hessian matrix-based image enhancement method, wherein the Hessian matrix at each point of the image I(x) is $$\nabla^2 I(x) = \begin{bmatrix} I_{xx}(x) & I_{xy}(x) \\ I_{yx}(x) & I_{yy}(x) \end{bmatrix},$$

eigenvalues of the Hessian matrix at each point is calculated as $\lambda_1$ and $\lambda_2$, $$\lambda_{12} = \begin{cases} |\lambda_2|\left(1 + \frac{\lambda_1}{|\lambda_2|}\right) = |\lambda_2| + \lambda_1 & \text{if } \lambda_2 \leq \lambda_1 \leq 0 \\ |\lambda_2|\left(1 - \alpha\frac{\lambda_1}{|\lambda_2|}\right) = |\lambda_2| - \alpha\lambda_1 & \text{if } \lambda_2 < 0 < \lambda_1 < \frac{|\lambda_2|}{\alpha}, \\ 0 & \text{otherwise} \end{cases}$$

$$R(x) = \lambda_{12}(x)$$

is defined as the enhanced image, and α=0.25. Otsu adaptive threshold segmentation is applied to the enhanced image within each 32*32 window of a crack detected by the small-scale deep learning model, and a binary image img2 of the crack is obtained after uniting.

23) The binary image img1 and the binary image img2 are united to obtain an output crack binary image for the 224*224 window.

24) The output binary image results for all detected 224*224 windows containing cracks in the first step are united to obtain a preliminary crack extraction result for the whole image.

As an improvement of the present invention, the fine crack detection method based on deep learning, image segmentation and image reconstruction in step 3) is specifically as follows:

As the preliminarily-extracted crack binary image will contain a lot of noise information, the proposed image segmentation method based on a single-pixel crack skeleton is utilized to segment the preliminarily-extracted crack image at two levels, and an image reconstruction method, in connection with deep learning, is utilized to perform single-factor analysis on the segmented cracks to determine whether they are cracks, ultimately realizing the fine extraction of cracks.

The image segmentation method based on a single-pixel skeleton is conducted at two levels. The skeleton is first segmented according to connectivity, portions of the crack binary image that each corresponds to one independent connected component are extracted respectively, and then each remaining connected component is further segmented into independent portions with endpoint and node information collected from the single-pixel crack skeleton, and the first level of segmentation can be implemented by utilizing the connectivity of the initial crack binary image.

The second level of segmentation is specifically as follows:

A pixel on the skeleton that has only one of its eight neighbors on the skeleton is defined as an endpoint, and a pixel that has more than three of its eight neighbors on the skeleton is defined as a node, and on the basis of each independent connected component skeleton, the binary image output at the previous level is further segmented, with the endpoint and node information of a single pixel, into independent portions as outputs of this level, and the method for segmenting an independent connected component includes the following operations:

a. An eight-neighbor rule is utilized to identify endpoints and nodes on the skeleton, segmentation is terminated when there are only endpoints and no node on the skeleton, and the corresponding regions in the initial crack binary image are directly output.

b. The nodes on the connected component are deleted, by utilizing the endpoint and node information, to obtain independent skeleton segments, the length of each skeleton segment is calculated, and a threshold T is set as 32.

c. As other interferences on cracks often occur in the form of skeleton branches, for each segmented skeleton segment that contains one endpoint for the original skeleton, regardless of whether the length of the skeleton segment is lower than the threshold, a circle is drawn, with a radius of ten pixels and a center at the node, to obtain intersections with other skeleton branches of the same node, the region of the skeleton is determined with the angle bisector of each branch of the node and the outline of the initial crack binary image, and independent crack binary regions are obtained from segmentation and filling by a region growing algorithm.

d. For a skeleton segment has a length greater than the threshold T and two ends as nodes on the original skeleton, a circle is drawn, with a radius of ten pixels and a center at the node, to obtain intersections with other skeleton branches of the same node, the region of the skeleton is determined with the angle bisector of the node and the outline of the original binary image, and independent crack binary regions are obtained from segmentation and filling by a region growing algorithm.

e. If the length of the extracted skeleton is less than the threshold, the center of the skeleton is determined, and an initial crack binary image having a length and width as T around the center of the skeleton segment is directly captured as a segmented image.

A single-factor analysis is performed, by the image reconstruction method in combination with deep learning, on the segmented cracks, and a new fine detection image that contains separately-segmented crack information but contains no other interference information needs to be constructed for fine crack detection of each segmented independent region.

The specific method for constructing a fine detection image in step 3) is as follows:

a. After an initial crack binary image is obtained, the region corresponding to the initial crack binary image is removed from the original image.

b. The removed region of the original image is filled with the average value of the three-channel (RGB) values of pixels around each connected component of the initial crack binary image, and the edge is removed by median filtering to construct a new image.

c. For images segmented from a crack binary image based on a single-pixel skeleton at two levels, binary connected components are extracted, and the length of a bounding rectangle of each connected component is calculated.

d. A fine detection image is constructed with the original image, the new image and the range of the bounding rectangles of connected components, that is, each independent segmented crack binary image region is filled with the value of the original image and a region outside the segmented crack binary image region is filled with the value of the new image to obtain a constructed detection image, wherein the specific rule is as follows: if the length of the bounding rectangle is less than or equal to 32, a detection image is constructed with the original image and the new image within a range of 32*32 around the center, and is scaled to the size of 224*224; if the length of the bounding rectangle is greater than 32 but less than 96, a new image is constructed within a range of the length of the bounding rectangle around the center, and is scaled to the size of 224*224; if the length of the bounding rectangle is greater than 96 but less than 224, a 224*224 image is directly constructed around the center with the new image and the original image; and if the length of the bounding rectangle is greater than 224, a detection image is constructed within a range of 224 pixels expanding outwardly from the bounding rectangle around the center.

Figure 5:
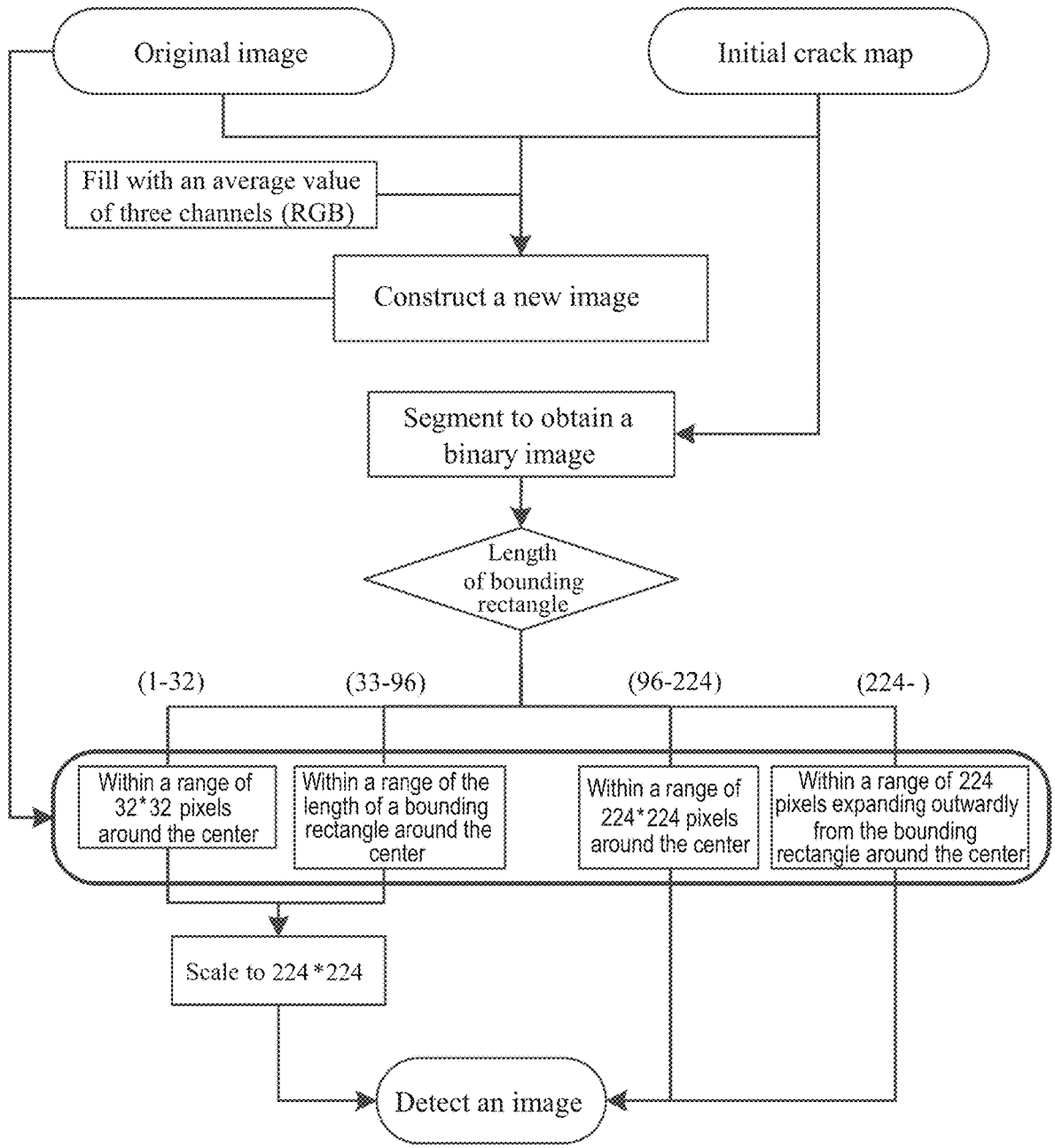
FIG. 5 is a diagram of a method for constructing a fine detection image in fine crack detection according to the present invention.

After a constructed detection image for the segmented crack is obtained, detection based on deep learning is performed once again to carry out single-factor analysis on the segmented cracks, thus achieving the purpose of fine extraction. The constructed detection images are also divided into two levels according to the two levels of the segmentation method based on the single-pixel skeleton, and the method for constructing a fine detection image is shown in FIG. 5. The specific method for scanning and detecting the constructed fine detection image with deep learning is as follows:

a. For images constructed at two levels, if the image size is less than or equal to 224*224*3, the image is enlarged to the size of 224*224*3, and then detected with a deep learning model to directly determine whether a crack is contained therein.

b. For constructed detection images with a size larger than 224*224*3, corresponding crack skeletons are extracted, and grids equidistantly spaced by 32 pixels in x and y directions are constructed, and a new image is scanned and detected with a intersections of a skeleton and a checkerboard as a center, wherein some of the intersections should be removed, so that the distance between every two intersections is larger than 16 pixels. The detection results are analyzed statistically. For constructed images at the first level, if the proportion of detection results representing that cracks are contained is greater than 0.2, then it is considered that cracks are contained. For constructed images at the second level, if the proportion of detection results representing that cracks are contained is greater than 0.8, then it is considered that cracks are contained.

After three steps including crack range detection based on multi-scale deep learning, preliminary crack binary image extraction and fine crack detection, a crack binary image having high precision, high accuracy and high recall can be obtained.

Example 2

Figure 6:
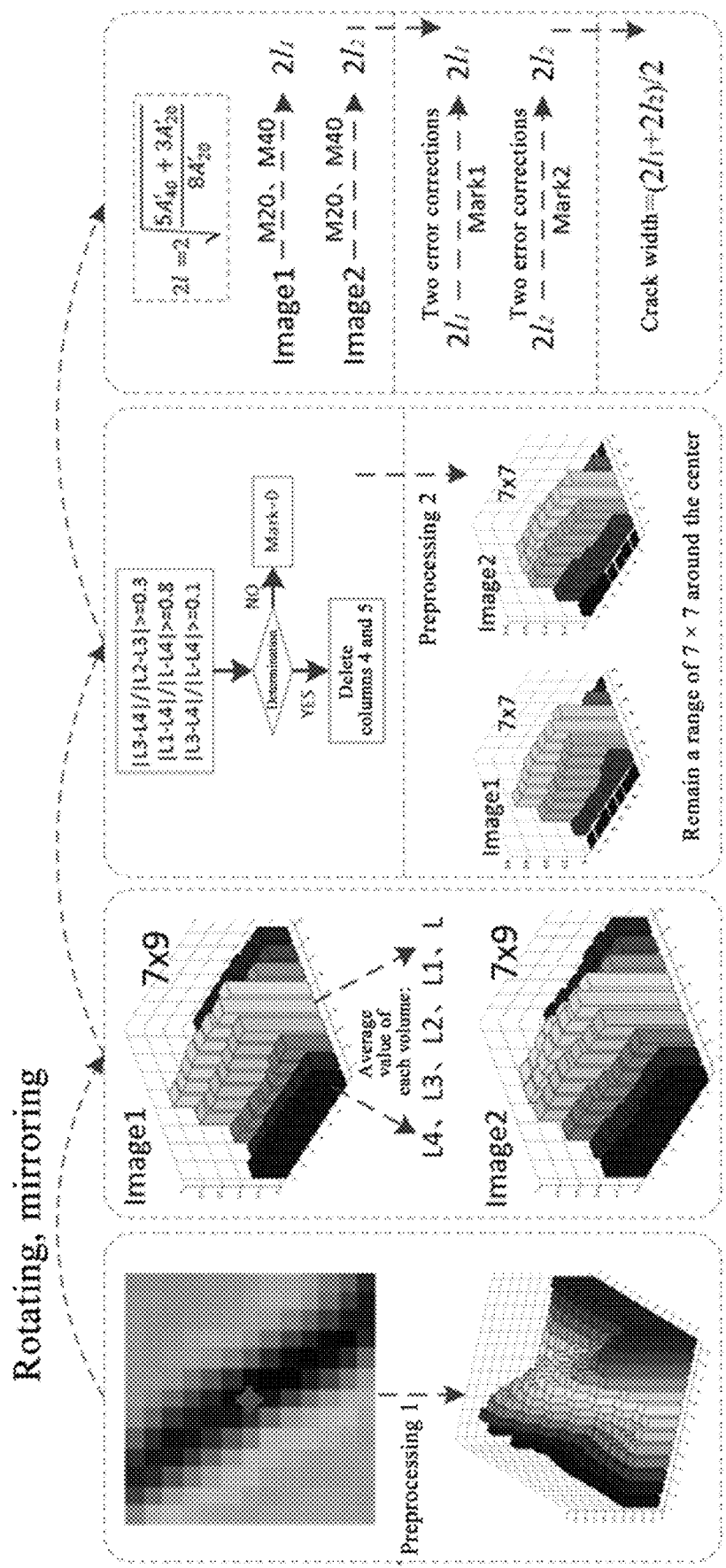
FIG. 6 is a diagram of a method for calculating widths of micro-cracks in an image based on a single-pixel skeleton and Zernike orthogonal moments according to the present invention.

A method for precisely measuring crack widths based on a single-pixel crack skeleton and Zernike orthogonal moments Conventional methods for calculating crack widths, which calculate the distance between two pixels by "pixel counting", works badly in calculating the width of a crack less than 5 pixels. Therefore, for cracks smaller than 5 pixels in images, the present invention proposes a method for calculating crack widths based on a single-pixel skeleton and Zernike orthogonal moments, as shown in FIG. 6.

The method for calculating crack widths based on a single-pixel skeleton and Zernike orthogonal moments utilizes a single-pixel skeleton to determine a rotation angle for an image. The image at this point is rotated, symmetrized and mirrored to obtain two images symmetrical with respect to the y coordinate axis. The second-order orthogonal moment $A'_{20}$ and the fourth-order orthogonal moment $A'_{40}$ are calculated respectively for the two symmetrical images by utilizing Orthogonal moment templates. The widths of the two symmetrical images are respectively calculated by a formula $$2l = 2\sqrt{\frac{5A'_{40} + 3A'_{20}}{8A'_{20}}}.$$

An average value is taken as crack width (unit: pixel) at this point after two error corrections are performed, and a final width of the crack at this point is obtained according to a pixel resolution (mm/pixel). It is worth noting that the method proposed by the present invention actually calculates an average width of a crack within an orthogonal moment template range at a certain point on an image.

1) A single-pixel crack skeleton around a width calculation point is extracted, a rotation angle is determined for the image, an image within a range of 13*13 pixels around the width calculation point is captured, and preprocessing 1 is performed to obtain a gray-scale image (0-1) of the image, a matrix, with all elements of 13*13 being 1, is subtracted from the gray-scale image, so that the gray value of a crack pixel in the image is high and the gray value of a background pixel is low, and the maximum gray value MAX is recorded.

2) The image is rotated according to the skeleton direction, mirroring operations are respectively performed, with the column where the accumulated gray value of cracks is the highest after rotation (i.e., the brightest column) as a central column, to obtain two symmetrical images, and smooth filtering is vertically applied to the two images.

3) It is checked whether the images obtained from mirroring meet requirements for calculation (assuming that the line width is 5 and the brightest is column 2, if one of the images does not meet conditions for calculation after mirroring, further processing is required). The average gray value within the range of a central column template is set as L, and the average gray value of each column on either side of the central column is set as L1, L2, L3 and L4 in sequence, wherein three conditions are set as: |L4−L3|/|L2−L3|>=0.3, |L1−L4|/|L−L4|>=0.8, and |L4−L3|/|L−L4|>=0.1. If all the three conditions are met, the central column and one column on the left side of the central column are deleted, and Mark=2 is recorded, otherwise, Mark=0 is recorded, and preprocessing 2 is performed: a minimum gray value MIN within a range of 7*7 around the image center is found, and the MIN is subtracted from the image gray to construct a new image.

Figure 8:
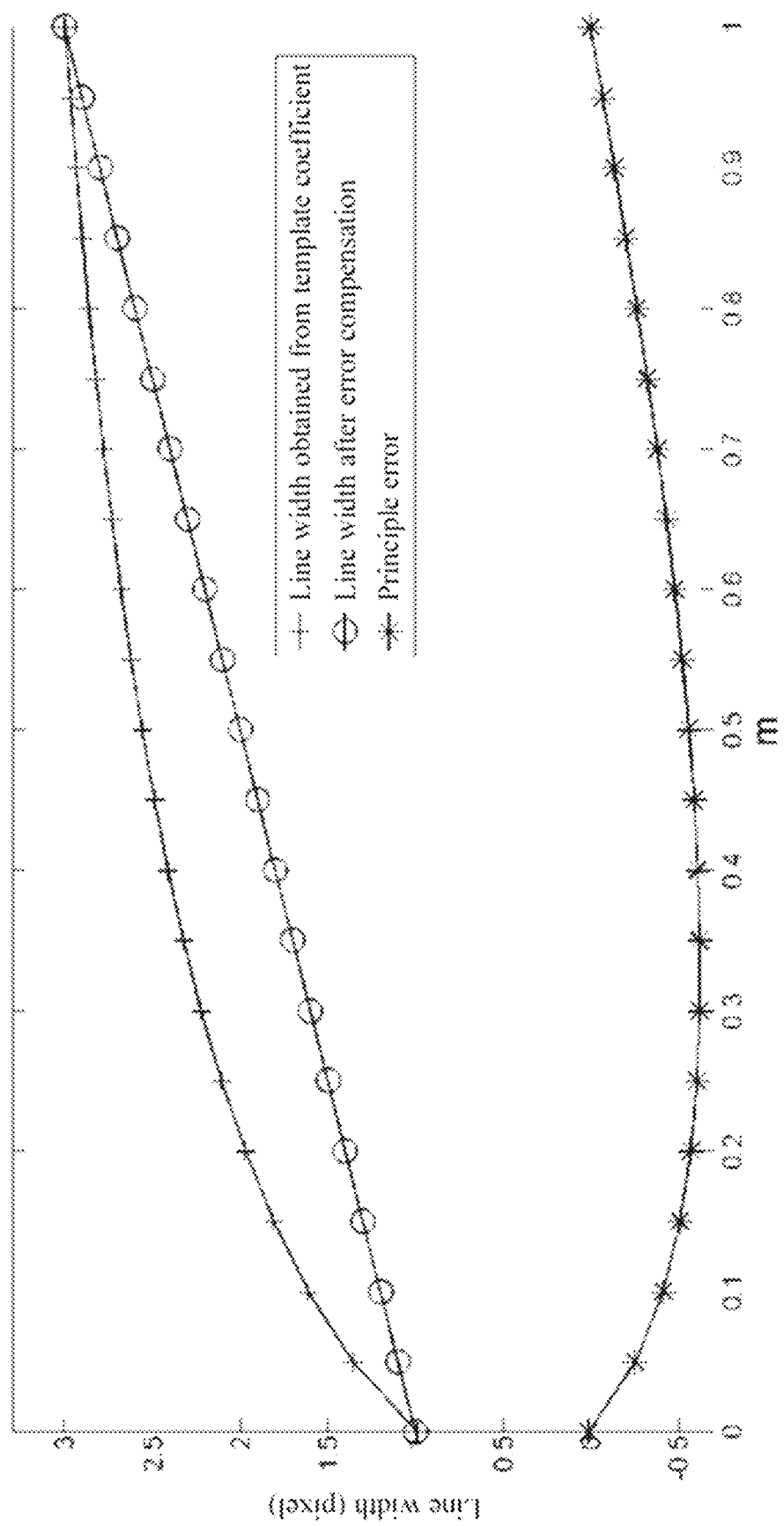
FIG. 8 is a graph of the first error correction (calculating principle errors by interpolation) in crack width measurement according to the present invention.

4) The existing orthogonal moment templates M20 and M40 as shown in FIG. 7 are used instead of the formula to calculate corresponding orthogonal moments and thus calculate the width of a crack in the image; the first error correction is as follows: principle error correction values are calculated by interpolation according to the value of m=L1/L with reference to FIG. 8; the second error correction is as follows: the average gray value within the range of the central column template of the image is divided by the maximum gray value MAX of the original image subtracted by the recorded minimum gray value MIN to obtain a correction factor, and a Mark value is added to the corrected value to obtain a final crack width of each mirror image; and then an average value of the calculated widths of the two mirror images after the error corrections is taken as a final crack width.

Example 3

Figure 1:
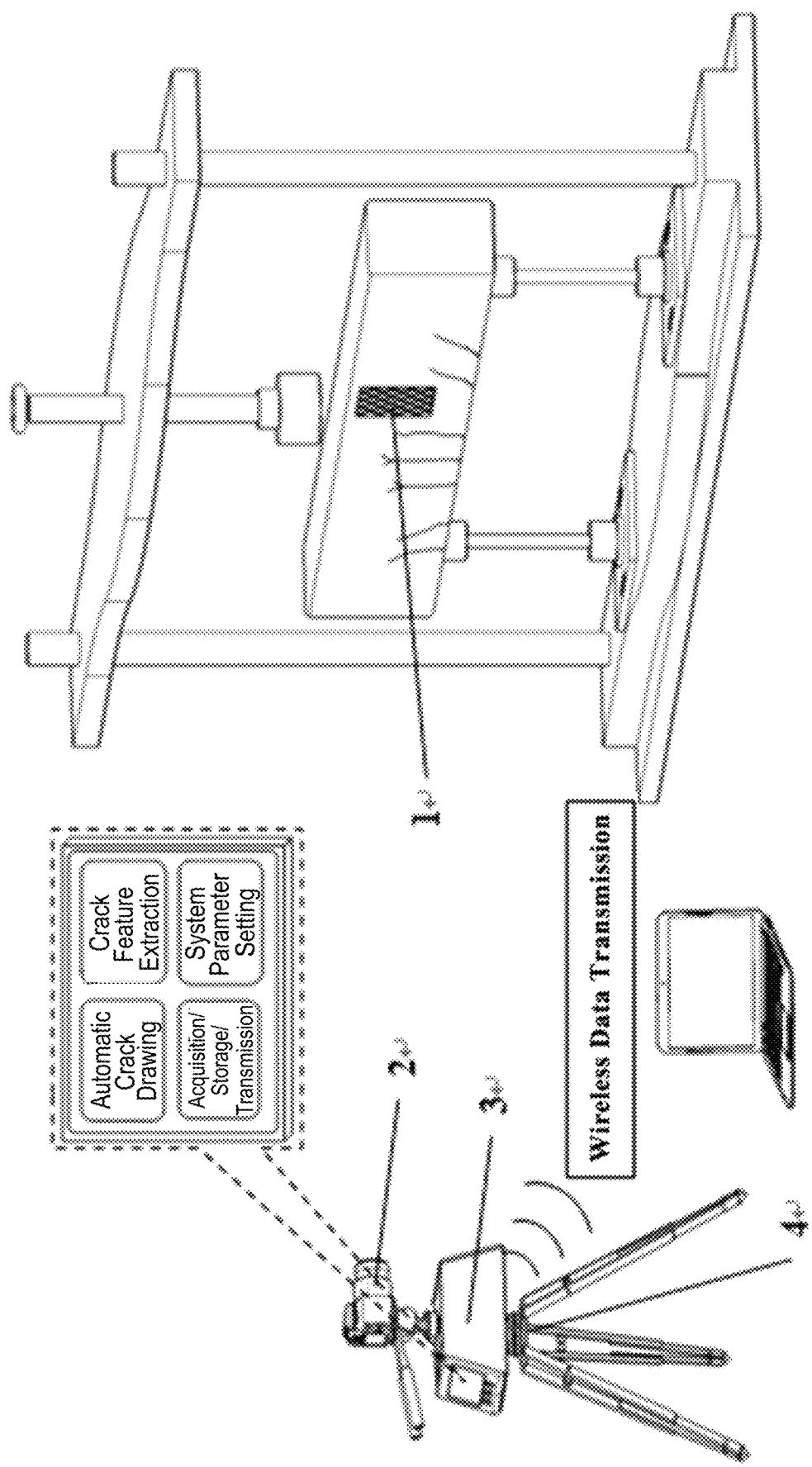
FIG. 1 is a conceptual diagram of a method and device for automatically drawing structural cracks and precisely measuring widths thereof according to the present invention.
Figure 2:
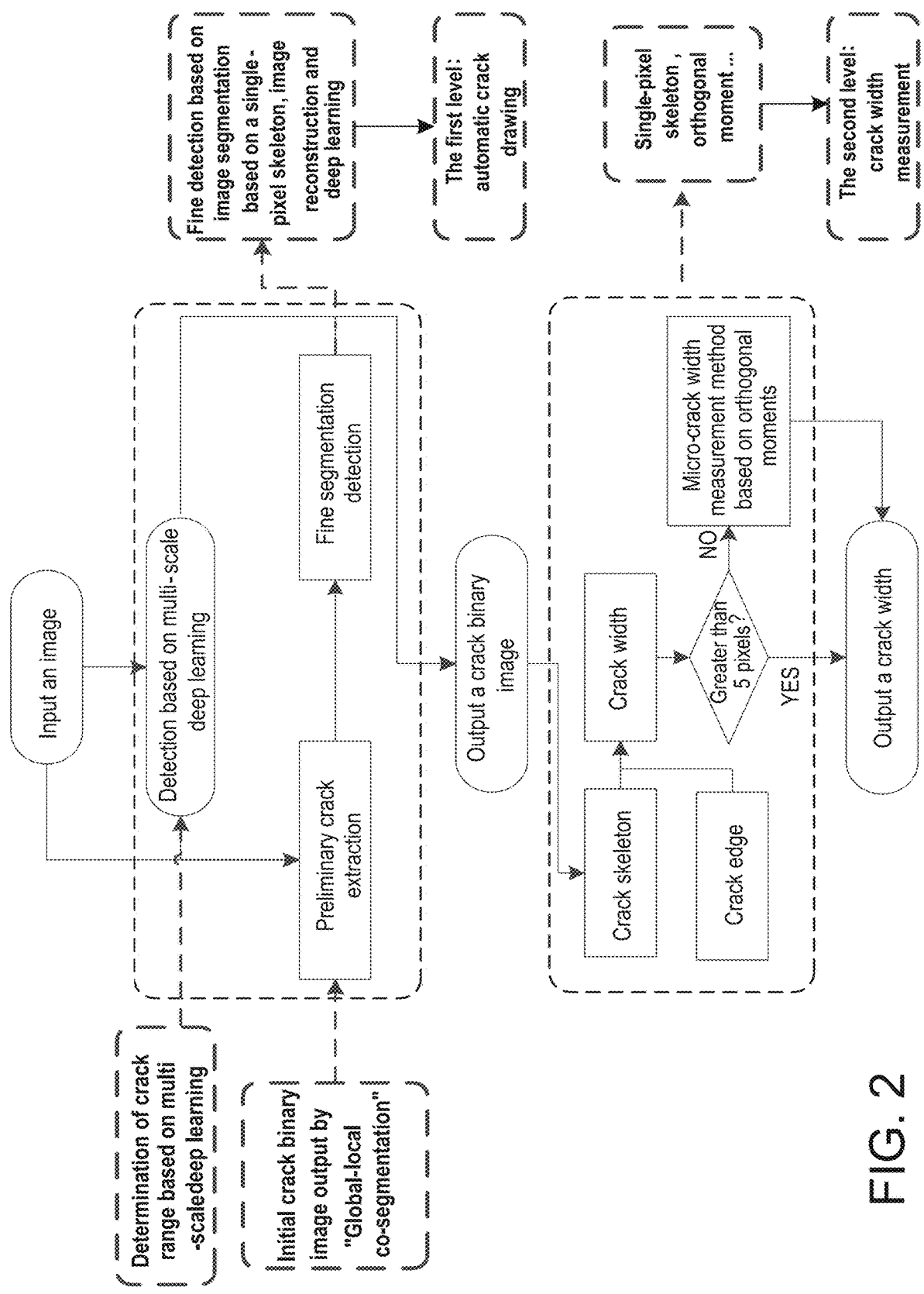
FIG. 2 is an overall technical roadmap according to the present invention.

A device for automatically drawing cracks of a concrete specimen and measuring widths thereof in a laboratory As shown in FIG. 1, the device comprises an image calibration module 1, an image acquisition module 2, an image processing system 3, and a camera tripod 4.

The device for automatically drawing structural cracks and precisely measuring widths thereof can rapidly and automatically draw structural cracks on a surface and precisely measure crack widths.

The image calibration module 1 is configured to correct the pose of a camera, calculate the resolution of an image, and paste a plurality of manually-printed checkerboards with a known size on the surface of a concrete specimen; the image acquisition module 2 composed of a single lens reflex camera is mainly configured to acquire a high-resolution image of the concrete specimen for image processing in the next step; and the image processing system 3 is embedded with an automatic crack drawing algorithm module, a crack feature analysis algorithm module, a calculation result storage module and a wireless transmission module, wherein the wireless transmission module is configured to wirelessly transmit a detection result and an original image to a client.

The automatic crack drawing algorithm module comprises a module for crack range detection based on multi-scale deep learning, a module for preliminary crack extraction based on deep learning, median filtering and Hessian matrix-based linear enhancement, and a module for fine crack detection based on deep learning, image segmentation and image reconstruction, and can rapidly and automatically draw the acquired image with high precision, high accuracy and high recall, wherein the information of both macro-cracks and micro-cracks in the image is drawn.

The crack feature analysis algorithm module is configured to calculate crack widths, and includes the method for calculating crack widths based on a single-pixel skeleton and Zernike orthogonal moments proposed by the present invention, and this method can also achieve higher calculation precision for micro-cracks smaller than 5 pixels in an image, obviously superior to conventional algorithms in terms of calculation precision.

Application Example 1

The large-scale deep learning model with an input of 224*224*3 pixels used in the present invention adopted the disclosed GoogLeNet model. There were 1000 types of output layers in the original network, while there were two types of output layers in a modified network, i.e., a crack type and a non-crack type. A transfer learning strategy and a self-constructed 224*224*3 image crack database were utilized to train the model. The deep learning model with an input of 32*32*3 pixels used in the present invention adopted the disclosed ResNet 20 model, and like the modified network, the original network had two types of output layers, i.e., the crack type and the non-crack type. A transfer learning strategy and a self-constructed 32*32*3 image crack database were utilized to train the model.

Before testing, manually printed checkerboards were pasted on the surfaces or the same plane of a tested concrete specimen according to the area thereof. The checkerboard size selected in this example was 4 cm*4 cm, and the side length of each checker was 1 cm. The pasted checkerboards were utilized to calibrate the pose of a camera, and the pose of the camera was adjusted so that each point on a checkerboard extracted from an image by a Harris corner detection method could be maintained as a square on the image.

After the installation of the device was completed, a complete data processing flow for each acquired image should comprise: scanning and detecting with deep learning models to roughly determine crack ranges in the image; preliminarily extracting a crack binary image; finely extracting a crack binary image; outputting width information of each manually-selected measurement point; and saving the original image and the output crack information.

Automatic Drawing of Crack Binary Image

Step 1, Crack range determination based on multi-scale deep learning The trained large-scale deep learning model with an input of 224*224*3 pixels was utilized to scan and detect by sliding windows on the acquired image, to check whether there were cracks in the image, and to roughly determine crack ranges in the image, and then marking was performed; and the trained small-scale deep learning model with an input of 32*32*3 pixels was utilized to scan each window of 224*224 pixels marked in the previous step in a moving manner, and marking was performed.

Step 2, Preliminary crack extraction The three-channel (RGB) original image was converted into a gray-scale image, each crack-contained 224*224 image marked in step 1 was processed by large-scale median filtering and then was subtracted from the original image to obtain a new image. Otsu adaptive threshold segmentation was applied to the new image to obtain a crack binary image img1. Within the range of each image of 224*224 pixels marked in step 2, the image was processed by small-scale median filtering and then was subtracted from the original gray-scale image to obtain a new gray-scale image, then 1-scale Hessian-based linear enhancement was applied to the new gray-scale image to obtain an enhanced image. Within the range of each 32*32 window marked in step 1, Otsu adaptive threshold segmentation was applied to the enhanced image, and then uniting operation was performed to obtain a crack binary image img2. All the crack binary images img1 and the crack binary images img2 were united to obtain an initial crack binary image.

Step 3, Fine crack extraction

Image thinning was applied to the initial crack binary image obtained in step 2 to obtain a crack skeleton with a single-pixel width, and the specific steps were as follows:

a. Zhang's fast parallel thinning algorithm was first employed to thin the initial crack binary image.

b. The texture thinned in the previous step was not a single pixel, because some of the points that should be deleted did not meet the deletion condition of Zhang's thinning algorithm. Eight neighbors of each of these points were coded in a binary manner, and the coded neighbors were converted into decimal forms to obtain numbers 65, 5, 20, 80, 13, 97, 22, 208, 67, 88, 52, 133, 141 and 54.

c. The eight neighbors of a target point were coded in a binary manner sequentially around a target point, and if the coding conforms to the aforementioned deletion feature, then the target point will be deleted to ensure the single-pixel property of an output target.

d. The eight-neighbor rule was utilized to identify endpoints (one pixel of its eight neighbors was 1) and nodes (three or four pixels of its eight neighbors were 1) on the skeleton, and the positions of the nodes were saved.

e. The identified nodes were deleted, and the crack skeleton was segmented into segments. Each segment contained branches of one or two endpoints, the lengths of the skeleton branches were calculated, and those branches that were smaller than 20 pixels were considered as burrs and removed. If a node had two skeleton branches and the lengths of the two branches, i.e., a distance from the node to a respective end point, both were less than 20 pixels, then the longer one remained.

f. With the identified nodes, the segmented skeletons were connected and the isolated points were contained in the skeleton to obtain a crack skeleton of a single-pixel width, and then the endpoint and node information of the skeleton was re-identified.

After the single-pixel crack skeleton was obtained, the skeleton was first segmented according to connectivity, portions of the crack binary image that each corresponds to one independent connected component were extracted respectively. A detection image was constructed for each portion in combination with the original image (RGB), and it was detected whether a crack was contained in the connected component once again by deep learning, and the connected components that did not contain cracks were deleted.

Then, all the remaining connected components contained crack information, but some connected components might contain both cracks and noise. With the endpoint and node information collected from the single-pixel crack skeleton, each remaining connected component was further segmented into independent portions, and a detection image was constructed for each portion in combination with the original image (RGB). It was detected whether a segmented portion contained crack information once again by utilizing a deep learning model, and an output crack binary image was obtained after the fine detection was completed.

Measurement of Crack Width at One Point in Image

Step 1, The crack width at one point in the image was measured, and the normal direction of the crack was determined with the single-pixel crack skeleton at this point. As the output crack binary image result would be affected by the size of a median filtering template used in the preliminary crack extraction, crack width L (unit: pixel) was roughly determined by utilizing the intersections of the normal direction and the edge of the output final crack binary image. Within a rectangular range with a side length of 5*L around the center of a measurement point, median filtering based on a template size of 2*L was applied, and the filtered image was subtracted from the original image to obtain a new image. With Canny operator, the distance between the two intersections of the normal at this point and the edge of the new image was detected to determine crack width (unit: pixel) at this point. The pixel resolution of the image was calculated from the number of pixels occupied by the checkerboard of a known size in the image, and the crack width (unit: pixel) was multiplied by the pixel resolution (mm/pixel) to obtain crack width (unit: mm). If the calculated width result was greater than 5 pixels, it was considered to meet the precision requirement.

Step 2, For a crack having a width less than 5 pixels calculated in step 1, the width was calculated according to the crack width identification method based on Zernike orthogonal moments proposed in the present invention.

Application Example 2

In an example where an experiment of destroying a concrete beam was conducted, cracks on the concrete beam were automatically drawn and widths of these cracks were measured according to the present invention.

(1) Experimental Preparation

Figure 9:
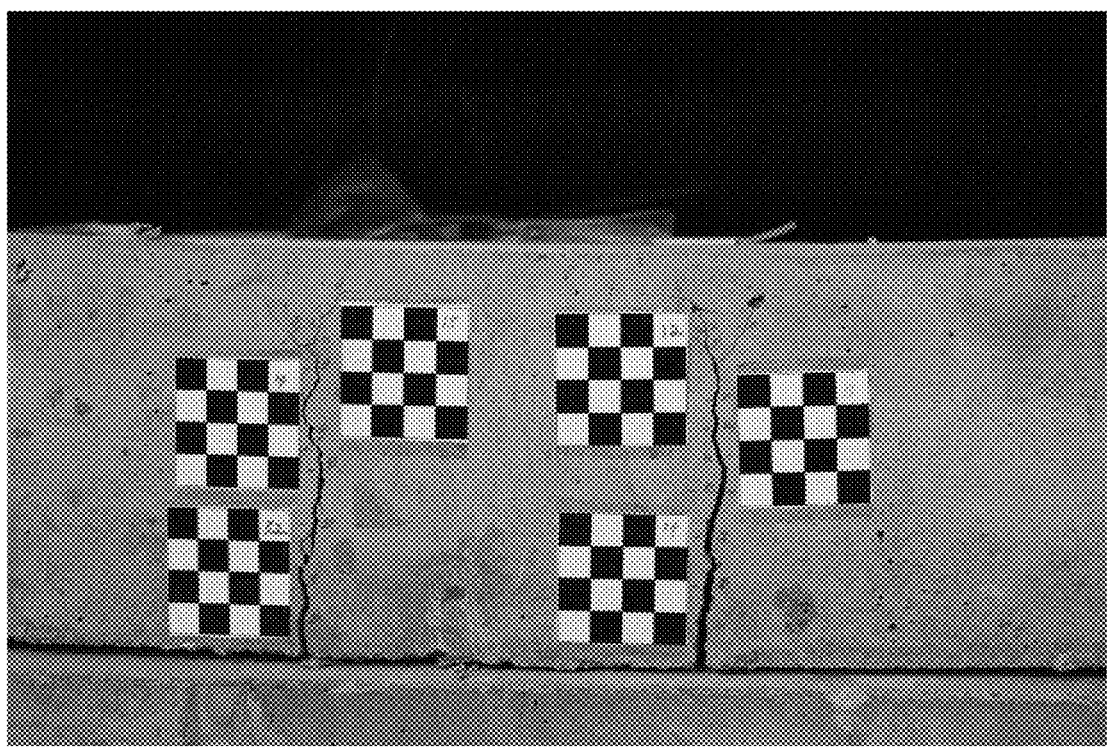
FIG. 9 is an image of cracks on a concrete specimen shot by a camera in the example according to the present invention.

Checkerboard marks were pasted on a concrete surface, and meanwhile, the crack width measurement points were marked manually. In the present example, a plurality of checkerboards were pasted on the concrete surface, and the crack width measurement points were numbered manually to increase the identification difficulty for the algorithm, as shown in FIG. 9. The camera was fixed by utilizing a tripod, and the pose of the camera was corrected with the pasted checkerboards so that the camera could directly shoot the front surface of the concrete beam, and a test system was connected to achieve the real-time calculation and real-time analysis.

(2) Scanning and Detection Based on Deep Learning

Figure 10:
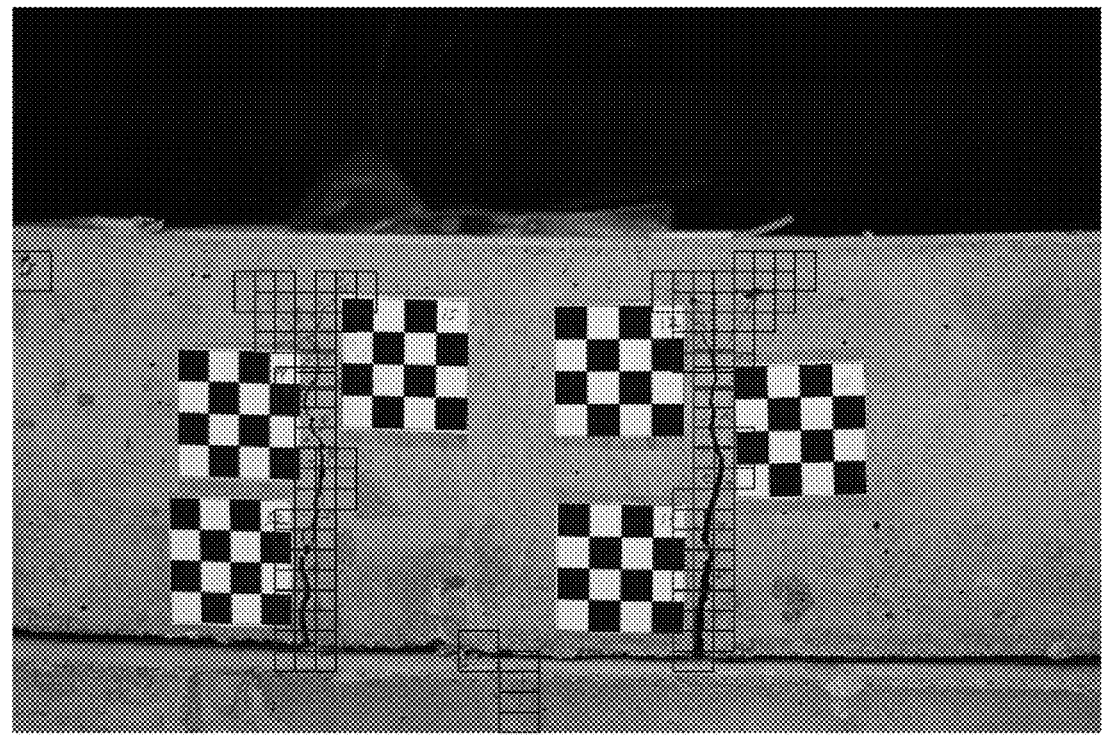
FIG. 10 is a result image of crack ranges scanned and detected by utilizing deep learning (224*224*3) according to the present invention.

An image was scanned and detected by utilizing a trained large-scale deep learning model with an input of 224*224*3. If the input image of FIG. 9 was detected, the output result was shown in FIG. 10.

(3) Extraction of Initial Crack Binary Image Based on Deep Learning

Figure 11:
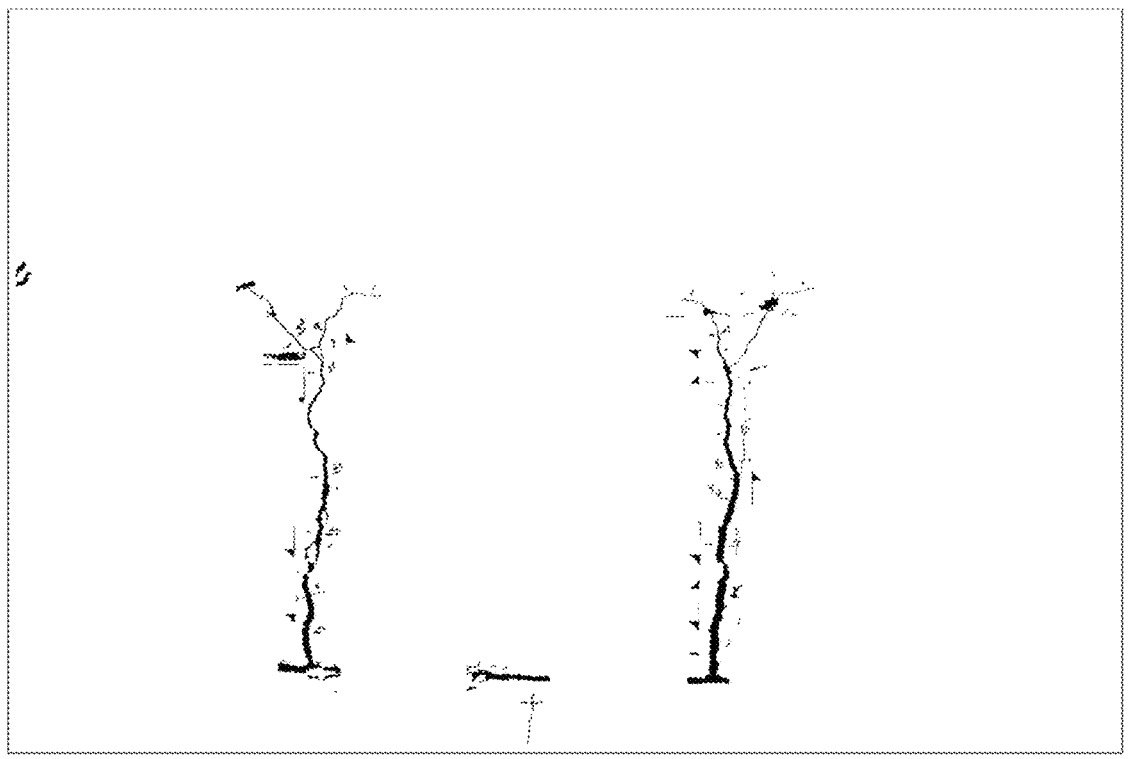
FIG. 11 is a result image of preliminary crack binary image extraction according to the present invention.

For each 224*224 window containing a crack detected in the previous step, a 32*32*3 small-scale deep learning model was employed to scan and detect each 224*224 image in a moving manner. The image was processed by large-scale median filtering, and the filtered image was subtracted from the original image to obtain a new image, and Otsu adaptive threshold segmentation was applied to the new image to obtain a crack binary image img1. Also, the image was processed by small-scale median filtering, and the filtered image was subtracted from the original image to obtain a new image, the linear portion of the new image was then enhanced by a Hessian matrix-based image enhancement method, Otsu adaptive threshold segmentation was applied to the enhanced image within each 32*32 window of a crack detected by the small-scale model, and a crack binary image img2 was obtained after uniting. The binary image img1 and the binary image img2 are united to obtain an output crack binary image for the 224*224 window. The above process was repeated, and the output binary image results for all detected 224*224 windows containing cracks in the previous step were united to obtain a preliminary crack extraction result for the whole image, as shown in FIG. 11.

(4) Fine Detection of Crack Binary Image Based on Deep Learning

Figure 12:
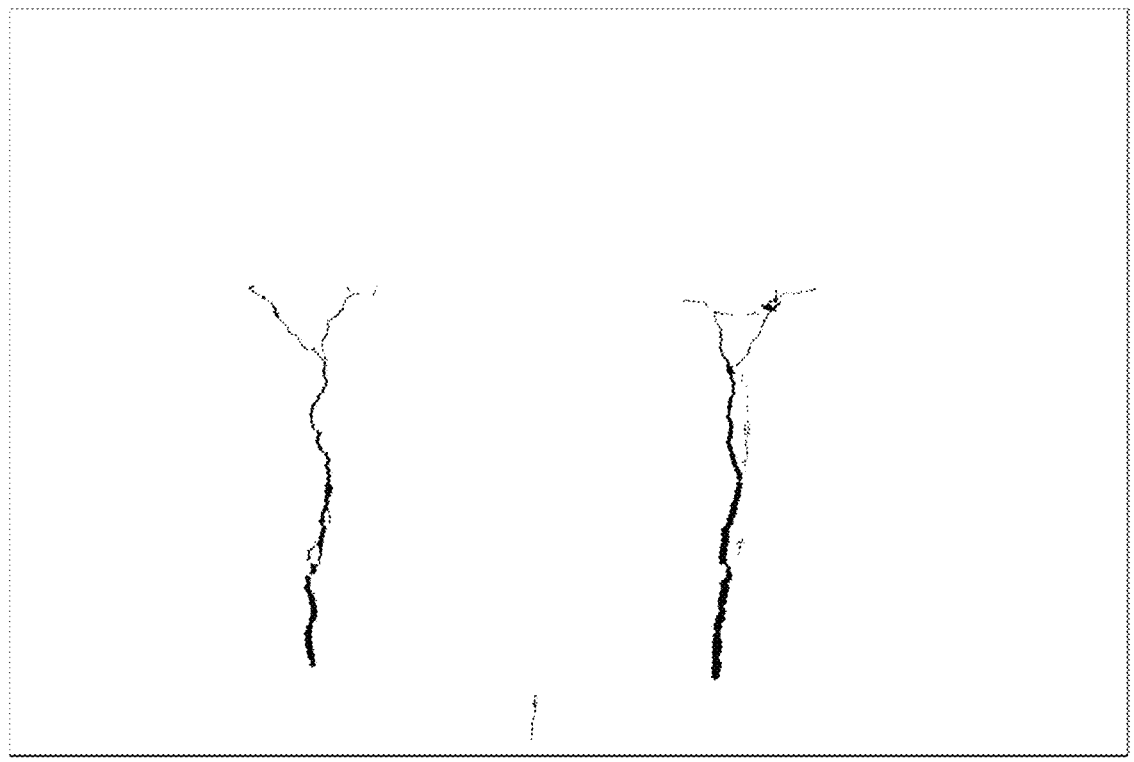
FIG. 12 is a result image of fine crack binary image extraction according to the present invention.

After the previous step, the single-pixel crack skeleton of the crack binary image was first extracted, and on this basis, the preliminarily-extracted crack binary image was segmented at two levels. The initial crack region was removed from the original image, and the removed region was filled with an average value of the pixels around each connected component to construct a new image. The crack binary image was segmented by utilizing the single-pixel crack skeleton, a corresponding fine detection image was constructed according to the original image and the new image, it was detected whether there was a crack once again by utilizing a trained deep learning model, and the fine detection result was output, as shown in FIG. 12.

Figure 13:
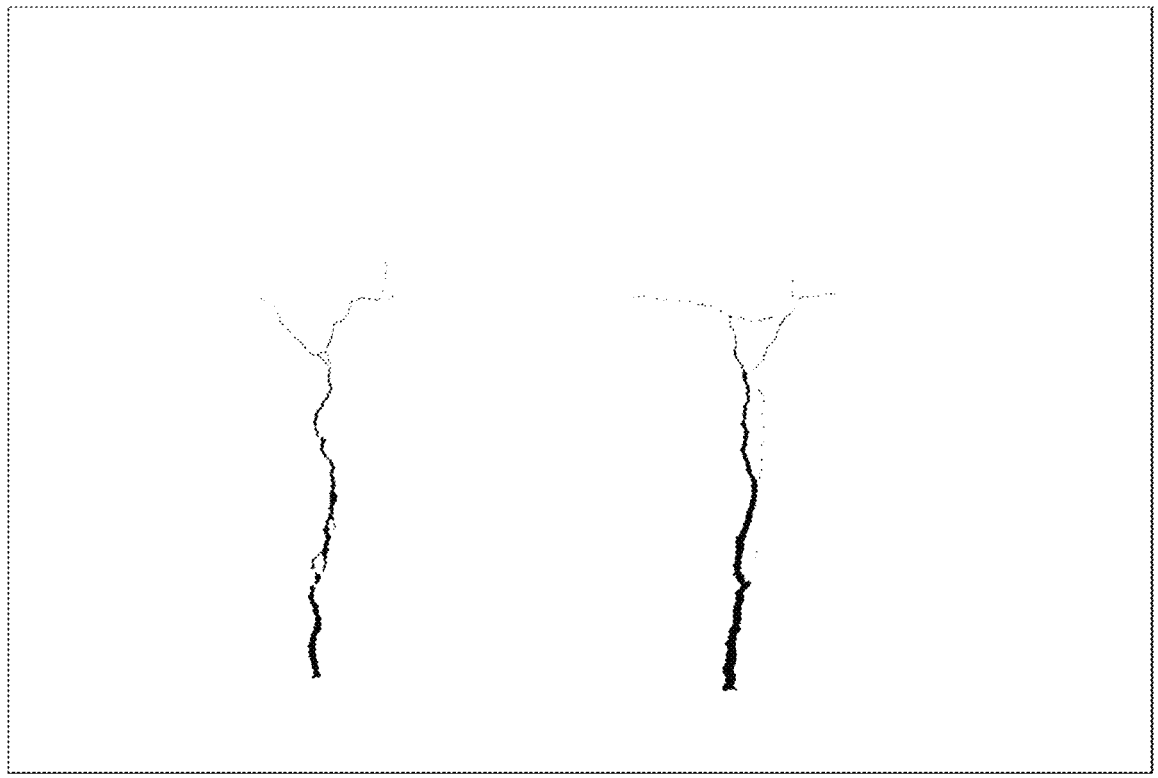
FIG. 13 is a result image of manually drawing a crack binary image according to the present invention.

The manually-drawn crack binary image as shown in FIG. 13 was compared with the crack binary image result output by the method provided in the present invention. The image was segmented into equidistantly spaced squares, each of 25*25 pixels, and 38,400 squares in total.

The condition of the manually-drawn crack in each square was compared with that of the automatically-drawn crack to determine the detection precision.

TP (True Positive): The number of squares containing a crack in both the manually-drawn crack image and the automatically-drawn crack image;

TN (True Negative): The number of squares containing no crack in both the manually-drawn crack image and the automatically-drawn crack image;

FP (False Positive): The number of squares containing no crack in the manually-drawn crack image but containing a crack in the automatically-drawn crack image; and FN (False Negative): The number of squares containing a crack in the manually-drawn crack image but containing no crack in the automatically-drawn crack image;

wherein three indexes were set:

accuracy=$(TP+TN)/(TP+FN+FP+TN)$, precision=$TP/(TP+FP)$, and recall=$TP/(TP+FN)$.

The extracted crack result was analyzed, and the corresponding accuracy, precision and recall were 99.82%, 93.45% and 92.9% respectively, indicating that the method provided in the present invention could still maintain high accuracy, high precision and high recall under the interference of the complex artificial marks.

Figure 14:
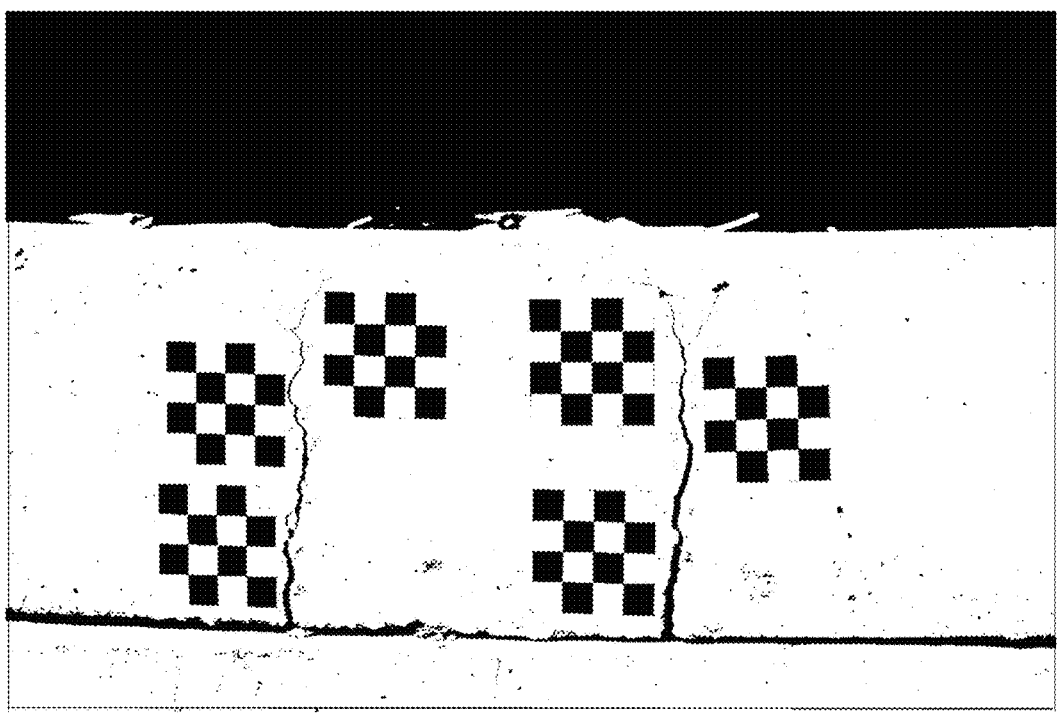
FIG. 14 is a result image of detection after directly applying Otsu adaptive threshold segmentation according to the present invention.

FIG. 14 is a detection result after directly applying Otsu adaptive threshold segmentation.

Figure 15:
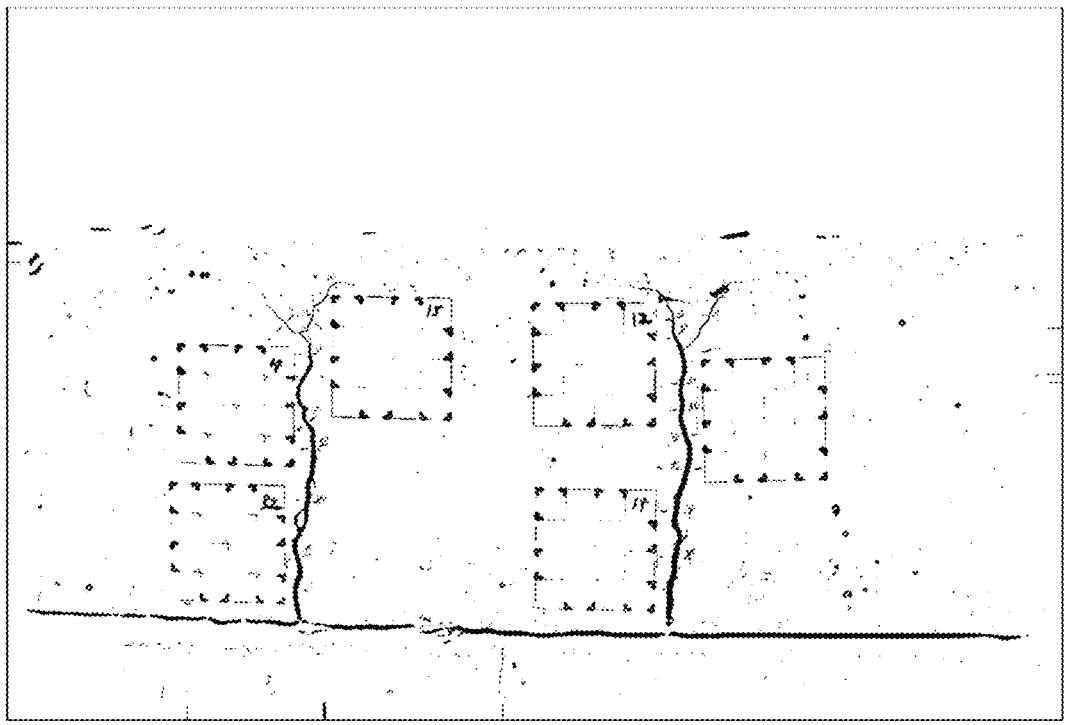
FIG. 15 is a result image of Otsu adaptive threshold segmentation detection after Hessian matrix-based linear enhancement according to the present invention.

FIG. 15 is a detection result after Otsu adaptive threshold segmentation following Hessian matrix-based image enhancement applied to the original image under the scale of n=8.

As shown in FIG. 14 and FIG. 15, it can be seen that the method provided by the present invention is significantly superior to a conventional method.

(5) Crack Width Measurement

The normal direction of the crack was determined by the single-pixel crack skeleton at the crack width measurement point, and width L was roughly determined by utilizing the intersections of the normal direction and the edge of the output crack binary image. Within a rectangular range with a side length of 5*L around the center of a measurement point, median filtering based on a template size of 2*L was applied, and the filtered image was subtracted from the original image to obtain a new image. With Canny operator, the two intersections of the normal at this point and the edge of the new image were detected to determine crack width (unit: pixel) at this point. If the width was greater than 5 pixels, it was considered to meet the precision requirement. The pixel resolution of the image was calculated by utilizing the checkerboard calibrator of a known size in the image, and the crack width (unit: pixel) was multiplied by the pixel resolution (mm/pixel) to obtain crack width. For a crack having a calculated width less than 5 pixels, the width at this point was calculated according to the proposed crack width identification method based on a single-pixel skeleton and Zerniek orthogonal moments.

Figure 16:
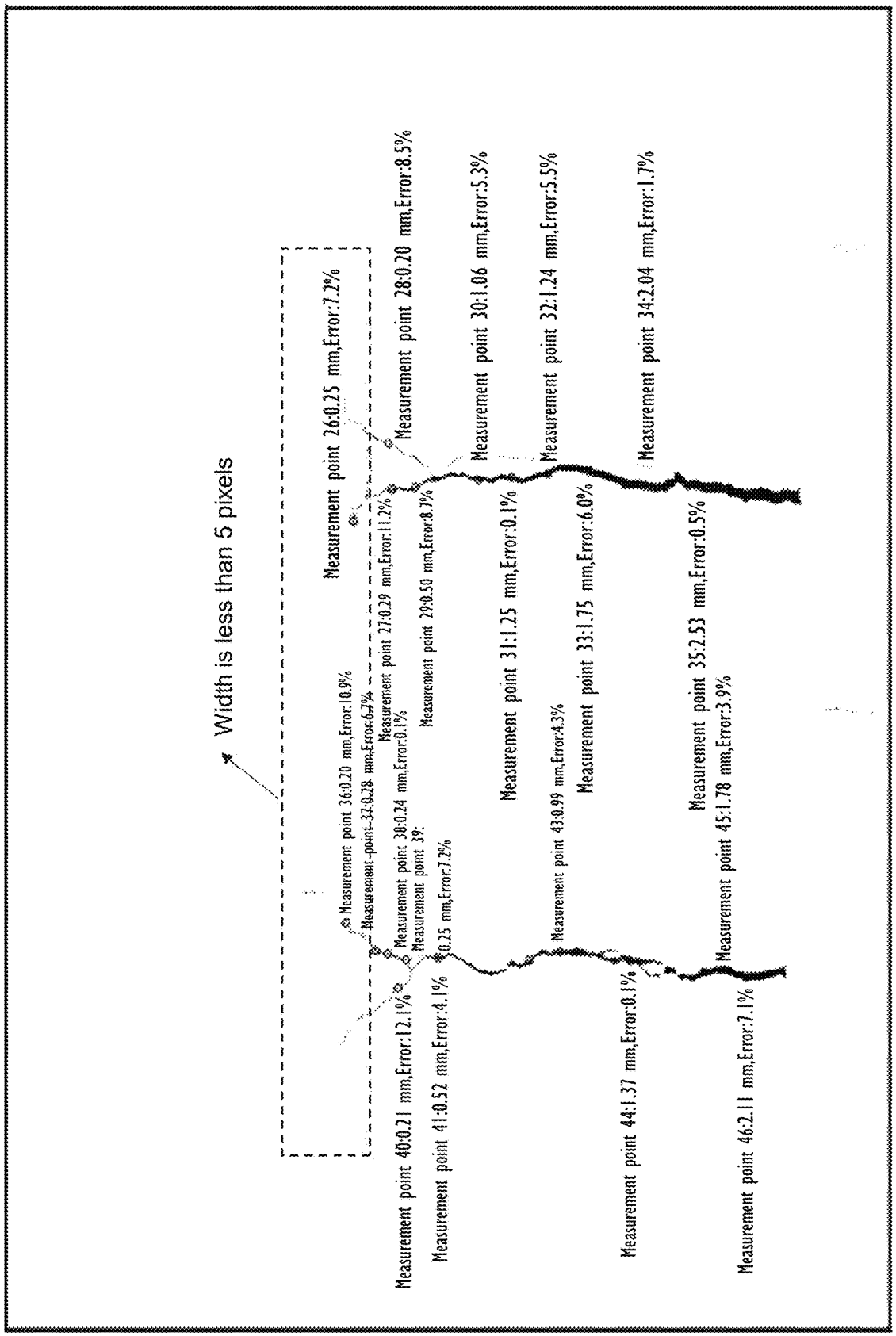
FIG. 16 is a result image of crack width measurement according to the present invention.

Crack width manually measured by using a crack width gauge with a precision of 0.0125 mm was compared with that of the proposed method, and the comparison result was shown in FIG. 16.

The advantages of the method provided by the present invention in measuring micro-crack widths in an image, over a conventional measurement method by "calculating the distance between two intersections", were further verified. A cracked concrete beam was adopted as an experimental object, crack images were captured with a camera from the front at different distances, and 248 width calculation points were selected for cracks smaller than 5 pixels in different images. A pixel resolution at the position of a crack was calculated according to a checkerboard near the crack. Meanwhile, images were acquired by a crack width gauge, the crack on an image acquired by the crack width gauge was drawn manually, and an average width of the crack in a corresponding length range was calculated as a true value.

Since the method provided in the present invention actually calculated the average width of the crack at a certain point on the image within the orthogonal moment template range (7*7 pixels), the average width calculated by the method provided in the present invention was compared with average width values calculated within orthogonal moment template ranges corresponding to crack binary images extracted under the following twelve working conditions.

Working condition 1: An image was converted into a gray-scale image. After the gray-scale image was smoothed, Ostu threshold segmentation was directly applied to the smoothed image to obtain a binary image, and the average width of a crack was calculated within the range of 7*7 pixels along the length direction of the crack at this point.

Working condition 2: An image was converted into a gray-scale image, and median filtering was applied to the gray-scale image. Then the filtered image was subtracted from the original gray-scale image to obtain a new image. Ostu threshold segmentation was applied to the new image to obtain a binary image, and the average width of a crack was calculated within the range of 7*7 pixels along the length direction of the crack at this point.

Working conditions 3 to 6: An image was converted into a gray-scale image, and median filtering was applied to the gray-scale image. Then the filtered image was subtracted from the original gray-scale image to obtain a new image. linear enhancement was applied to the new image, with a scale of n=1, n=2, n=4 and n=10 for work conditions 3, 4, 5, 6 respectively. Ostu threshold segmentation was applied to the enhanced image to obtain a binary image, and the average width of a crack was calculated within the range of 7*7 pixels along the length direction of the crack at this point.

Working condition 7: An image was converted into a gray-scale image. The edge was detected by Canny operator, and image closing operation was performed to obtain a binary image. The average width of a crack was calculated within the range of 7*7 pixels along the length direction of the crack at this point.

Working condition 8: An image was converted into a gray-scale image. The edge was detected by Canny operator, image closing operation was performed to obtain a new image, and the edge extracted by Canny operator was then subtracted from the new image to obtain a binary image. The average width of a crack was calculated within the range of 7*7 pixels along the length direction of the crack at this point.

Working condition 9: The results of working condition 7 and working condition 8 were averaged.

Working condition 10: An image was converted into a gray-scale image, and median filtering was applied to the gray-scale image. Then the filtered image was subtracted from the original gray-scale image to obtain a new image.

The edge of the new image was detected by Canny operator, and then image closing operation was performed to obtain a binary image. The average width of a crack was calculated within the range of 7*7 pixels along the length direction of the crack at this point.

Working condition 11: An image was converted into a gray-scale image, and median filtering was applied to the gray-scale image. Then the filtered image was subtracted from the original gray-scale image to obtain a new image. The edge of the new image was detected by Canny operator. The image closing operation was performed, and the edge extracted by Canny operator was then subtracted from the image resulting from image closing operation to obtain a binary image. The average width of a crack was calculated within the range of 7*7 pixels along the length direction of the crack at this point.

Working condition 12: The results of working condition 10 and working condition 11 were averaged.

Error statistics was performed on the results calculated by different methods, and the error statistics results were shown in Table 1.

TABLE 1

Comparative Statistical Analysis of Proposed Methods

| Serial Number | Proposed Method | Working Condition 1 | Working Condition 2 | Working Condition 3 | Working Condition 4 | Working Condition 5 | Working Condition 6 |
|---|---|---|---|---|---|---|---|
| Expected Error | 8.34% | 22.95% | 18.36% | 16.50% | 14.31% | 59.39% | 66.03% |
| Standard Deviation of Errors | 6.32% | 19.36% | 14.19% | 8.56% | 11.70% | 28.54% | 29.78% |

| Serial Number | Working Condition 7 | Working Condition 8 | Working Condition 9 | Working Condition 10 | Working Condition 11 | Working Condition 12 |
|---|---|---|---|---|---|---|
| Expected Error | 55.78% | 16.60% | 21.87% | 52.88% | 16.60% | 19.37% |
| Standard deviation of errors | 24.11% | 8.21% | 16.89% | 24.22% | 12.25% | 17.08% |

Figure 17:
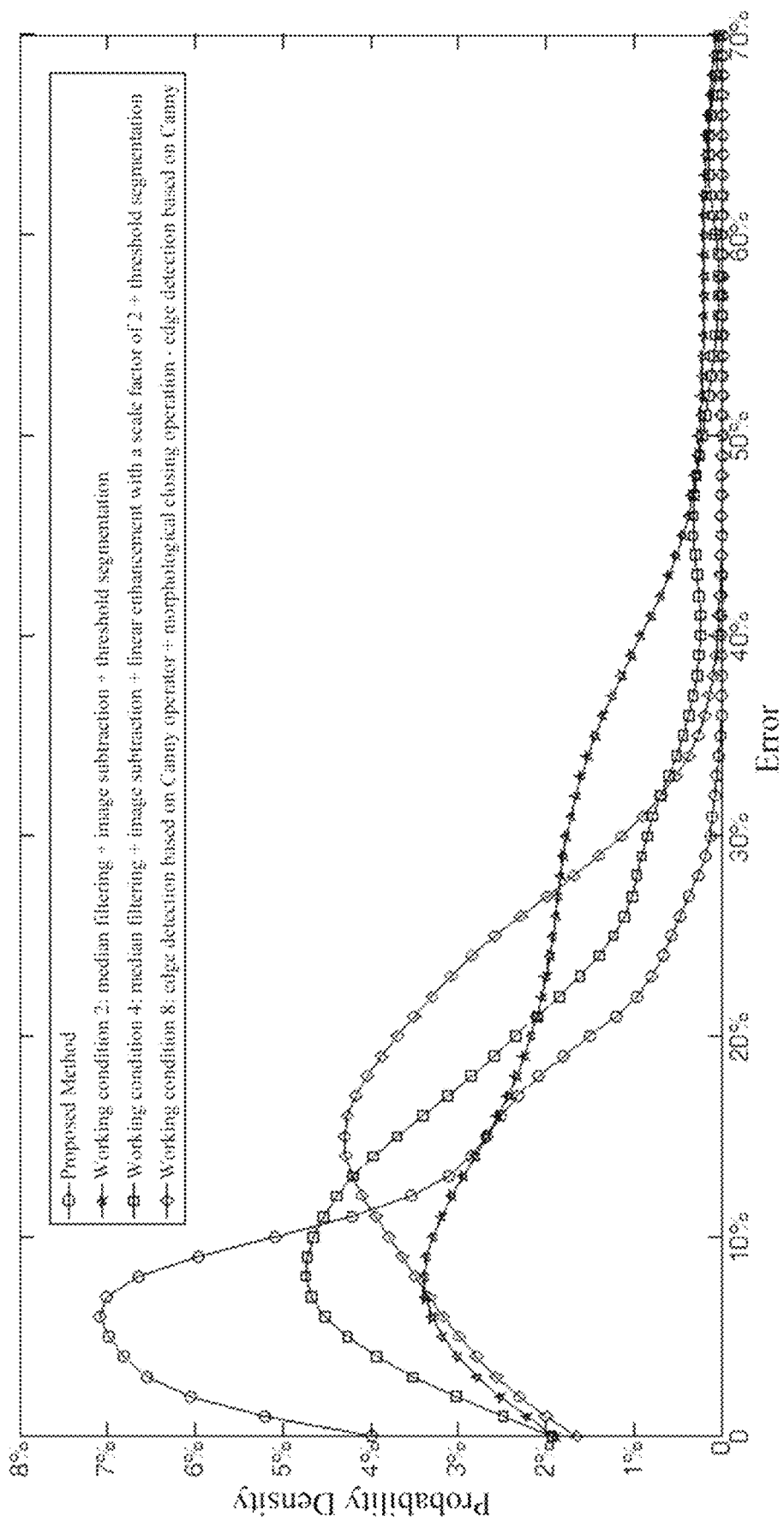
FIG. 17 is a graph of statistical comparative analysis for micro-crack width measurement results of different methods according to the present invention.

Working condition 1 and working condition 2 were grouped together as they adopted simple threshold segmentation. Working conditions 3 to 6 were grouped together as they adopted linear enhancements of different scales. Working conditions 8 to 12 were grouped together because the width was calculated after edge extraction based on Canny operator. The probability density distribution of the best performing working condition in each group was fitted correspondingly, and was compared with the result of the proposed method, and the result showed that the method provided in the present invention could achieve higher precision for micro-crack width measurement in comparison with the conventional width measurement methods. The comparison results were shown in FIG. 17.

To sum up, with the method and device for automatically drawing structural cracks and precisely measuring widths thereof provided in the present invention, a qualitative and quantitative analysis had been performed on cracks of the surface of a concrete specimen, and the process comprised: (1) rapidly and automatically drawing a crack binary image with high precision; and (2) precisely calculating crack width. Moreover, the method achieved significantly higher precision than conventional methods in measuring micro-cracks in an image.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method for automatically drawing structural cracks, comprising the following steps:
1) Detecting, by a crack detection method based on multi-scale deep learning, a crack range in an image using multi-scale deep learning;
2) Extracting, by a preliminary crack extraction method of "global-local co-segmentation" based on deep learning, median filtering and Hessian matrix-based linear enhancement, information of both macro-cracks and micro-cracks in the image; and
3) Effectively removing, by a fine crack detection method based on deep learning, image segmentation and image reconstruction, noise from the result.

2. The method for automatically drawing structural cracks according to claim 1, wherein the crack detection method based on multi-scale deep learning in step 1) comprises:
with deep learning models of multiple scales from large to small, the large-scale deep learning modules are first adopted to scan and detect the whole image; and on the basis that a crack range has been determined by the large-scale (224*224*3) deep learning modules, a small-scale (32*32*3) deep learning module is adopted to scan and detect the window of a crack detected by each large-scale deep learning module, wherein: for scanning and detection by the large-scale deep learning models, windows for each layer start from four right angles and slide to a center by 112 pixels each time in x and y directions, wherein the center refers to the intersection of x axis and y axis that lead to an image symmetry, and scanning windows for one layer are encrypted; and for each detected 224*224 window containing a crack, a small-scale deep learning model (32*32*3) is adopted to scan and detect each 224*224 image in a manner of sliding 16 pixels each time in x and y directions respectively.

3. The method for automatically drawing structural cracks according to claim 2, wherein the preliminary crack extraction method of "global-local co-segmentation" in step 2) comprises:
  21) within each 224*224 window of a crack detected by the large-scale deep learning model, an original image is converted into a gray-scale image and then processed by large-scale median filtering, the filtered image is subtracted from the original image to obtain a new image, and Otsu adaptive threshold segmentation is applied to the new image to obtain a binary image img1 of the crack;
  22) the original image is processed by small-scale median filtering, and the filtered image is subtracted from the original image to obtain a new image, and then the linear portion of the new image is enhanced by a Hessian matrix-based image enhancement method, wherein the Hessian matrix at each point of the image I(x) is $$\nabla^2 I(x) = \begin{bmatrix} I_{xx}(x) & I_{xy}(x) \\ I_{yx}(x) & I_{yy}(x) \end{bmatrix},$$

eigenvalues of the Hessian matrix at each point is calculated as $\lambda_1$ and $\lambda_2$, $$\lambda_{12} = \begin{cases} |\lambda_2|\left(1 + \frac{\lambda_1}{|\lambda_2|}\right) = |\lambda_2| + \lambda_1 & \text{if } \lambda_2 \leq \lambda_1 \leq 0 \\ |\lambda_2|\left(1 - \alpha\frac{\lambda_1}{|\lambda_2|}\right) = |\lambda_2| - \alpha\lambda_1 & \text{if } \lambda_2 < 0 < \lambda_1 < \frac{|\lambda_2|}{\alpha}, \\ 0 & \text{otherwise} \end{cases}$$

$$R(x) = \lambda_{12}(x)$$

is defined as the enhanced image, and $\alpha$=0.25, Otsu adaptive threshold segmentation is applied to the enhanced image within each 32*32 window of a crack detected by the small-scale deep learning model, and a binary image img2 of the crack is obtained after uniting;
  23) the binary image img1 and the binary image img2 are united to obtain an output crack binary image for the 224*224 window;
  24) the output binary image results for all detected 224*224 windows containing cracks in the first step are united to obtain a preliminary crack extraction result for the whole image.

4. The method for automatically drawing structural cracks according to claim 3, wherein the fine crack detection method based on deep learning, image segmentation and image reconstruction in step 3) comprises:
  a proposed image segmentation method based on a single-pixel crack skeleton is utilized to segment the preliminarily-extracted crack image at two levels, and an image reconstruction method, in connection with deep learning, is utilized to perform single-factor analysis on segmented cracks to determine whether they are cracks, ultimately realizing the fine extraction of cracks,
  wherein the image segmentation method based on a single-pixel skeleton is conducted at two levels: the skeleton is first segmented according to connectivity, portions of the crack binary image that each corresponds to one independent connected component are extracted respectively, and then each remaining connected component is further segmented into independent portions with endpoint and node information collected from the single-pixel crack skeleton, and the first level of segmentation can be implemented by utilizing the connectivity of the initial crack binary image;
  the second level of segmentation comprises:
    a pixel on the skeleton that has only one of its eight neighbors on the skeleton is defined as an endpoint, and a pixel that has more than three of its eight neighbors on the skeleton is defined as a node, and on the basis of each independent connected component skeleton, the binary image output at the previous level is further segmented, with the endpoint and node information of a single pixel, into independent portions as outputs of this level, and the method for segmenting an independent connected component comprises the following operations:
    a. an eight-neighbor rule is utilized to identify endpoints and nodes on the skeleton, segmentation is terminated when there are only endpoints and no node on the skeleton, and the corresponding regions in the initial crack binary image are directly output;
    b. the nodes on the connected component are deleted, by utilizing the endpoint and node information, to obtain independent skeleton segments, the length of each skeleton segment is calculated, and a threshold T is set as 32;
    c. for each segmented skeleton segment that contains one endpoint for the original skeleton, regardless of whether the length of the skeleton segment is lower than the threshold, a circle is drawn, with a radius of ten pixels and a center at the node, to obtain intersections with other skeleton branches of the same node, the region of the skeleton is determined according to the angle bisector of each branch of the node and the outline of the initial crack binary image, and independent crack binary regions are obtained from segmentation and filling by a region growing algorithm;
    d. for a skeleton segment has a length greater than the threshold T and two ends as nodes on the original skeleton, a circle is drawn, with a radius of ten pixels and a center at the node, to obtain intersections with other skeleton branches of the same node, the region of the skeleton is determined according to the angle bisector of the node and the outline of the original binary image, and independent crack binary regions are obtained from segmentation and filling by a region growing algorithm;
    e. if the length of the extracted skeleton is less than the threshold, the center of the skeleton is determined, and an initial crack binary image having a length and width as T around the center of the skeleton segment is directly captured as a segmented image; and
  a single-factor analysis is performed, by the image reconstruction method in combination with deep learning, on the segmented cracks, and a new fine detection image that contains separately-segmented crack information but contains no other interference information needs to be constructed for fine crack detection of each segmented independent region.

5. The method for automatically drawing structural cracks according to claim 4, wherein the specific method for constructing a fine detection image in step 3) comprises:
  a. after an initial crack binary image is obtained, the region corresponding to the initial crack binary image is removed from the original image;

b. the removed region of the original image is filled with the average value of the three-channel (RGB) values of pixels around each connected component of the initial crack binary image, and the edge is smoothed by median filtering to construct a new image;
c. for images segmented from a crack binary image based on a single-pixel skeleton at two levels, binary connected components are extracted, and the length of a bounding rectangle of each connected component is calculated;
d. a fine detection image is constructed with the original image, the new image and the range of the bounding rectangles of connected components, that is, each independent segmented crack binary image region is filled with the value of the original image and a region outside the segmented crack binary image region is filled with the value of the new image to obtain a constructed detection image, wherein the specific rule is as follows: if the length of the bounding rectangle is less than or equal to 32, a detection image is constructed with the original image and the new image within a range of 32*32 around the center, and is scaled to the size of 224*224; if the length of the bounding rectangle is greater than 32 but less than 96, a new image is constructed within a range of the length of the bounding rectangle around the center, and is scaled to the size of 224*224; if the length of the bounding rectangle is greater than 96 but less than 224, a 224*224 image is directly constructed around the center with the new image and the original image; and if the length of the bounding rectangle is greater than 224, a detection image is constructed within a range of 224 pixels expanding outwardly from the bounding rectangle around the center.

* * * * *